(12) United States Patent
Kubota et al.

(10) Patent No.: US 8,900,876 B2
(45) Date of Patent: Dec. 2, 2014

(54) ABNORMALITY-IDENTIFYING METHOD AND ANALYZER

(75) Inventors: Kiyotaka Kubota, Tokyo (JP); Yukihiro Furusawa, Tokyo (JP); Koji Fujimori, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 524 days.

(21) Appl. No.: 12/422,592

(22) Filed: Apr. 13, 2009

(65) Prior Publication Data

US 2009/0257051 A1  Oct. 15, 2009

Related U.S. Application Data

(63) Continuation of application No. PCT/JP2007/065009, filed on Jul. 31, 2007.

(30) Foreign Application Priority Data

Oct. 13, 2006  (WO) .................. PCT/JP2006/320468

(51) Int. Cl.
*G01N 21/00* (2006.01)
*G01N 35/10* (2006.01)
*G01N 35/00* (2006.01)

(52) U.S. Cl.
CPC ...... *G01N 35/00623* (2013.01); *G01N 35/1004* (2013.01)

USPC .......................................... 436/164; 356/237.1

(58) Field of Classification Search
None
See application file for complete search history.

(56) References Cited

FOREIGN PATENT DOCUMENTS

| JP | 06-331630 | | 12/1994 | |
|---|---|---|---|---|
| JP | 09-210999 | * | 8/1997 | .................... 436/164 |
| JP | 2003-057248 | | 2/2003 | |
| JP | 2003-083988 | | 3/2003 | |
| JP | 2004-347385 | | 12/2004 | |

* cited by examiner

*Primary Examiner* — Robert Xu
(74) *Attorney, Agent, or Firm* — Kilpatrick Townsend & Stockton LLP

(57) ABSTRACT

Provided is an abnormality-identifying method for identifying an abnormality in an analyzer which analyzes a specimen based on optical measurement. The method includes firstly acquiring a reference value which is a measurement result obtained by using a low-concentration reagent containing a component in predetermined very low concentrations, secondly acquiring an abnormality-identification measurement value which is a measurement result obtained through an analysis process using a high-concentration reagent containing the component in predetermined high concentrations, and identifying an abnormality in an analysis process concerning removal of the high-concentration reagent based on whether the abnormality-identification measurement value is within an acceptable range set based on the reference value.

11 Claims, 21 Drawing Sheets

FIG.8

| IDENTIFICATION-DIRECTED BF CLEANING | ABNORMALITY-IDENTIFICATION MEASUREMENT VALUE | ABNORMAL | |
|---|---|---|---|
| FIRST BF CLEANING | 1.1 TIMES OF REFERENCE VALUE OR MORE | FIRST BF CLEANING | R1 |
| SECOND BF CLEANING | 1.1 TIMES OF REFERENCE VALUE OR MORE | SECOND BF CLEANING | R2 |
| FIRST BF CLEANING AND SECOND BF CLEANING | 1.2 TIMES OF REFERENCE VALUE OR MORE | FIRST BF CLEANING AND SECOND BF CLEANING | R3 |

T1

| ABNORMALITY-<br>IDENTIFICATION<br>MEASUREMENT VALUE | ABNORMAL |
|---|---|
| 1.1 TIMES OF<br>REFERENCE VALUE OR<br>MORE | PROBE CLEANING<br>DEFECT |

T2

ABNORMALITY-IDENTIFYING METHOD AND ANALYZER

CROSS-REFERENCE TO RELATED APPLICATIONS

This application is a continuation of PCT international application Ser. No. PCT/JP2007/065009 filed on Jul. 31, 2007 which designates the United States, incorporated herein by reference, and which claims the benefit of priority from PCT international application Ser. No. PCT/JP2006/320468, filed on Oct. 13, 2006, the entire contents of which are incorporated herein by reference.

BACKGROUND OF THE INVENTION

1. Field of the Invention

The present invention relates to identification of an abnormality in an analyzer which analyzes a specimen based on optical measurement.

2. Description of the Related Art

An analyzer can analyze a number of specimens at the same time, and further, can analyze many components immediately and accurately. The analyzer is used for various tests such as an immunological test, a biochemical test, and a blood-transfusion test. For example, the analyzer which performs the immunological test includes a reaction system in which the specimen is reacted with a reagent in a reaction vessel, a removal system in which unreacted substances are removed out of the reaction vessel, and a photometry system in which the amount of light emission from an immune complex obtained through reaction between the specimen and each reagent is measured. These systems are arranged on plural turntables, respectively. The analyzer further includes plural dispense/transfer systems which dispense or transfer the specimen, the reagent, or a reaction liquid into each of the systems. The analyzer performs immunological tests for various contents of the analysis (e.g., see Japanese Patent Application Laid-open No. 2003-83988).

Conventionally, the abnormality of the analyzer has been examined as follows. The analyzer performs a series of analysis processes, which are to be performed on an actual specimen, on a reference specimen with which a known analysis result should be produced, and then it is checked whether the analysis result produced by the analyzer is consistent with the known result. In other words, conventionally, when the analysis result obtained from the actual analysis of the reference specimen is consistent with the known analysis result, an operator of the analyzer determines that the analyzer functions normally whereas when the analysis result obtained from the actual analysis of the reference specimen is inconsistent with the known analysis result, the operator determines that the analyzer functions abnormally.

In the conventional method with the reference specimen, however, the operator can determine that there is an abnormality in the analyzer, but can hardly know which process or system of the analyzer exactly causes the abnormality. Especially, it is difficult to properly identify the abnormality in the analyzer which performs the immunological test, since the analyzer of the kind has a complex configuration in which various factors such as reaction time, a reagent to be used, a system to be used, and a timing to use the system are different depending on the contents of the analysis processes.

Further, conventionally, dispense accuracy of the dispense/transfer system is examined by dispensing the reagent which has predetermined absorbance characteristics into the reaction vessel, and referring to a measurement result obtained through a calorimetric method. The analyzer which performs the immunological test, however, does not include a calorimetric measurement unit. Therefore, to examine the dispense accuracy, the operator needs to perform the calorimetric measurement using a spectral photometer which is not included in the analyzer.

SUMMARY OF THE INVENTION

An abnormality-identifying method according to one aspect of the present invention for identifying an abnormality in an analyzer which analyzes a specimen based on optical measurement, includes firstly acquiring a reference value which is a measurement result obtained by using a low-concentration reagent containing a component in predetermined very low concentrations, secondly acquiring an abnormality-identification measurement value which is a measurement result obtained through an analysis process using a high-concentration reagent containing the component in predetermined high concentrations, and identifying an abnormality in an analysis process concerning removal of the high-concentration reagent based on whether the abnormality-identification measurement value is within an acceptable range set based on the reference value.

An analyzer according to another aspect of the present invention for analyzing a specimen based on optical measurement, includes a measurement unit that acquires a reference value which is a measurement result obtained by using a low-concentration reagent containing a component in predetermined very low concentrations, and acquires an abnormality-identification measurement value which is a measurement result obtained through analysis process using a high-concentration reagent containing the component in predetermined high concentrations, and an identifying unit that identifies an abnormality in an analysis process concerning removal of the high-concentration reagent based on whether the abnormality-identification measurement value is within an acceptable range set based on the reference value.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 8 is an exemplary table that is used in the abnormality-identifying process shown in FIG. 2;

DETAILED DESCRIPTION OF THE PREFERRED EMBODIMENTS

Embodiments of an analyzer according to the present invention which is used in various fields such as biochemical tests and blood-transfusion tests are described below with reference to accompanying drawings, taking as an example an analyzer which performs an immunological test such as an antigen-antibody reaction of tested blood in which magnetic particles are used as solid-phase carriers. These embodiments, however, do not limit the scope of the present invention. Same numerals are attached to same components.

Figure 1:
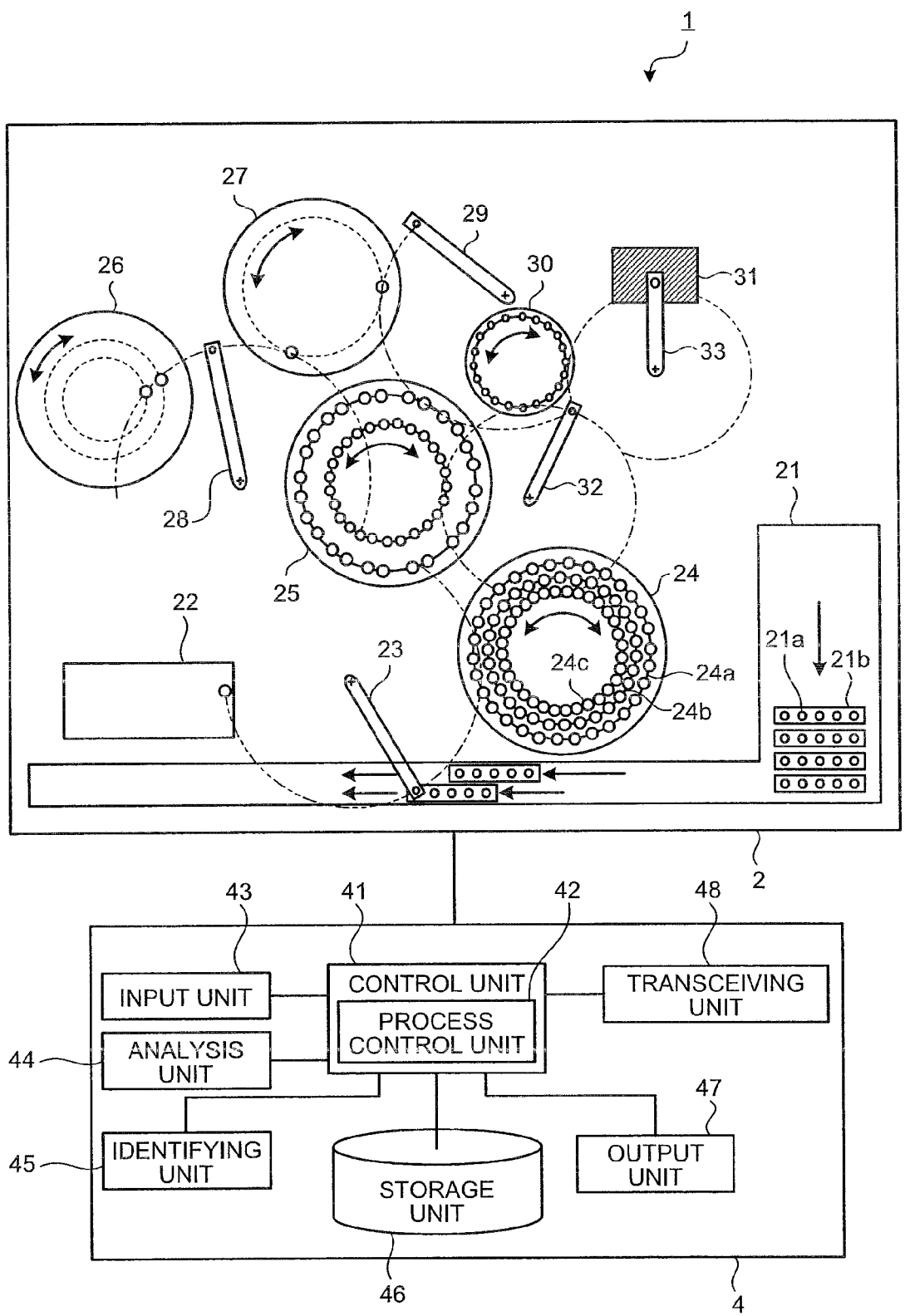
FIG. 1 is a schematic diagram of configuration of an analyzer according to a first embodiment of the present invention.

A first embodiment is described. A BF cleaning process is one of analysis processes performed on a specimen, and serves to remove unreacted substances in a reaction vessel. Described below is a case where presence/absence of defect in unreacted-substance removal in the BF cleaning process is identified. In the first embodiment, a reference value is set to a light-emission amount obtained from a low-concentration reagent containing antigens in very low concentrations. When the light-emission amount obtained after the BF cleaning from a high-concentration reagent containing antigens in high concentrations is equal to or higher than predetermined times the reference value, it is determined that there is a defect in the unreacted-substance removal in the BF cleaning process. FIG. 1 is a schematic diagram of a configuration of the analyzer according to the present embodiment. As shown in FIG. 1, analyzer 1 includes a measurement system 2 which measures light emission from a reaction between a specimen and a reagent, a control system 4 which controls the analyzer 1 as a whole including the measurement system 2 and analyzes a measurement result of the measurement system 2. The analyzer 1 automatically performs an immunological analysis on plural specimens through cooperation of these two systems.

The measurement system 2 includes a specimen transfer unit 21, a chip holder 22, a specimen dispense/transfer system 23, an immune reaction table 24, a BF table 25, a first-reagent holder 26, a second-reagent holder 27, a first-reagent dispense/transfer system 28, a second-reagent dispense/transfer system 29, an enzyme reaction table 30, a photometry system 31, a first-cuvette transfer system 32, and a second-cuvette transfer system 33. Each component of the measurement system 2 includes one or more units which perform a predetermined operation. Further, the control system 4 includes a control unit 41, an input unit 43, an analysis unit 44, an identifying unit 45, a storage unit 46, an output unit 47, and a transceiving unit 48. Each component of the measurement system 2 and the control system 4 is electrically connected with the control unit 41.

The measurement system 2 is described. The specimen transfer unit 21 holds plural specimen vessels 21a which contain specimens, and plural specimen racks 21b which are to be transferred sequentially in a direction along an arrow in the figure. The specimens contained in the specimen vessels 21a are blood, urine, or the like extracted from a donor who provides the specimens.

The chip holder 22 has a chip case in which plural chips are arranged, and the chip is provided out of the case. The chip is a disposal sample chip which is exchanged for each dispensing of the specimen. The chip is mounted on a distal end of a nozzle of the specimen dispense/transfer system 23 so that carryover in measurement of infectious diseases is prevented.

The specimen dispense/transfer system 23 includes an arm which can be moved up and down in vertical directions and rotated around a central axis, i.e., a vertical line crossing a proximal end thereof. A probe for sucking and dispensing the specimen is attached to a distal end of the arm. The specimen dispense/transfer system 23 makes the probe suck the specimen out of the specimen vessel 21a which has been transferred to a predetermined position by the specimen transfer unit 21, rotates the arm to dispense the specimen into a cuvette which has been transferred to a predetermined position by the BF table 25, and thus transfers the specimen into the cuvette on the BF table 25 at a predetermined timing.

The immune reaction table 24 includes reaction lines where the specimen is reacted with a predetermined reagent corresponding to an analysis point in each of the arranged cuvettes. The immune reaction table 24 can be rotated around a rotation axis, i.e., a vertical line crossing a center of the immune reaction table 24 for each of the reaction lines, and thus the cuvette arranged on the immune reaction table 24 is transferred to a predetermined position at a predetermined timing. As shown in FIG. 1, the immune reaction table 24 may form three reaction lines consisting of an outer circular line 24a for pretreatment and pre-dilution, a middle circular line 24b for the immune reaction of the specimen and a solid-phase carrier reagent, and an inner circular line 24c for the immune reaction of the specimen and a reference specimen.

The BF table 25 performs a BF cleaning process by which a predetermined cleaning fluid is discharged and sucked out to perform the BF (bound-free) separation, i.e., to separate unreacted substances of the specimen or the reagent. The BF table 25 can be rotated around a rotation axis, i.e., a vertical line crossing a center of the BF table 25 for each of the reaction lines, and thus the cuvette arranged on the BF table 25 is transferred to the predetermined position at the predetermined timing. The BF table 25 includes a magnetic collection system which magnetically collects the magnetic-particle carriers used for the BF separation, a BF cleaning nozzle which performs the BF separation, and a stir system which mixes up the carriers magnetically collected. The BF cleaning process performed by the BF table 25 includes a first BF cleaning process and a second BF cleaning process. The first BF cleaning process and the second BF cleaning process may employ different BF cleaning nozzle and magnetic collection system.

The first-reagent holder 26 can hold plural reagent vessels which contain the first reagent to be dispensed into the cuvette which is set on the BF table 25. The second-reagent holder 27 can hold plural reagent vessels which contain the second reagent to be dispensed into the cuvette which is set on the BF table 25. Both the first-reagent holder 26 and the second-reagent holder 27 can be rotated in a clockwise and counterclockwise direction by a driving system (not shown) to transfer a desired reagent vessel to a reagent sucking position of the first-reagent dispense/transfer system 28 and the second-reagent dispense/transfer system 29.

The first-reagent dispense/transfer system 28 includes an arm which can be moved up and down in vertical directions and rotated around a central axis, i.e., a vertical line crossing a proximal end thereof. A probe for sucking and dispensing the first reagent is attached to a distal end of the arm. The first-reagent dispense/transfer system 28 makes the probe suck the reagent out of the reagent vessel which has been transferred to a predetermined position by the first-reagent holder 26, and rotates the arm to dispense the reagent into a cuvette which has been transferred to a predetermined position by the BF table 25. A portion of the first-reagent dispense/transfer system 28 brought into contact with the reagent is cleaned every time the first-reagent dispense/transfer system 28 finishes dispensing the reagent.

The second-reagent dispense/transfer system 29 is configured similarly to the first-reagent dispense/transfer system 28. The second-reagent dispense/transfer system 29 makes the probe suck the reagent out of the reagent vessel which has been transferred to a predetermined position by the second-reagent holder 27, and rotates the arm to dispense the reagent into the cuvette which has been transferred to a predetermined position by the BF table 25. A portion of the second-reagent dispense/transfer system 29 brought into contact with the reagent is cleaned every time the second-reagent dispense/transfer system 29 finishes dispensing the reagent.

The enzyme reaction table 30 is the reaction line in which an enzyme reaction which involves light emission is caused in a cuvette into which the substrate solution has been dispensed. The photometry system 31 measures the light emission from the reaction liquid in the cuvette. To measure the light-emission amount, the photometry system 31 includes, for example, a photoelectron multiplier tube which detects a faint light emission from chemical luminescence. Further, the photometry system 31 holds an optical filter to lessen intensity of light depending on the intensity of light emission so that the intensity of light emission can be calculated correctly.

The first-cuvette transfer system 32 includes an arm which can be moved up and down in the vertical directions, and rotated around the central axis, i.e., the vertical line crossing the proximal end thereof. The arm transfers the cuvette containing a liquid to the predetermined positions of the immune reaction table 24, the BF table 25, the enzyme reaction table 30, and a cuvette supplying unit (not shown) and a cuvette disposal unit (not shown) at predetermined timing. Further, the second-cuvette transfer system 33 includes an arm which can be moved up and down in the vertical directions, and rotated around the central axis, i.e., the vertical line crossing the proximal end thereof. The arm transfers the cuvette containing the liquid to the predetermined positions of the enzyme reaction table 30, the photometry system 31, and the cuvette disposal unit (not shown) at predetermined timing.

The control system 4 is described. The control system 4 is realized by one or more computer systems, and connected with the measurement system 2. The control system 4 controls the operation processes of the measurement system 2, and analyzes the measurement result of the measurement system 2 by using various programs related to the processes of the analyzer 1.

The control unit 41 includes a CPU and the like which provide a control function, and controls the processes and the operations of the components of the analyzer 1. The control unit 41 performs a predetermined input/output control on information which is input/output to/from each of the components, and performs a predetermined information process on the information. The control unit 41 controls the analyzer 1 by reading out programs from a memory in the storage unit 46. The control unit 41 includes a process control unit 42.

The analyzer 1 acquires the light-emission amount of a low-concentration reagent containing antigens in very low concentrations, as a reference value. Further, the analyzer 1 acquires the light-emission amount of a high-concentration reagent containing antigens in high concentrations after the BF cleaning, as an abnormality-identification measurement value. Based on these values, the analyzer 1 identifies a fault in unreacted-substance removal in the BF cleaning process. The process control unit 42 controls each of the systems included in the measurement system 2 to acquire the reference value and the abnormality-measurement value for identifying the abnormality of the analyzer 1.

The input unit 43 is realized by a keyboard for inputting various information, a mouse for specifying an arbitrary position on a display screen of a display included in the output unit 47, and the like. The input unit 43 obtains various types of information for the analysis of the specimen, and instruction information and the like of the analysis operation from an outside. The analysis unit 44 performs an analysis process and the like on the specimen based on the measurement result obtained from the measurement system 2.

The identifying unit 45 determines whether there is an unreacted-substance removal defect in the BF cleaning process among the analysis processes performed on the specimen. The BF cleaning process serves to remove unreacted substances in the reaction vessel. The identifying unit 45 sets a reference value to the light-emission amount of the low-concentration reagent containing antigens in very low concentrations, and determines whether there is an unreacted-substance removal defect in the BF cleaning process or not based on the determination on whether the abnormality-identification measurement value, which is the light-emission amount of the high-concentration reagent containing antigens in high concentrations after the BF cleaning, is within an acceptable range, which is set based on the reference value.

The storage unit 46 includes a hard disk, which magnetically stores information therein, and a memory, which loads various programs related to a process of the analyzer 1 from the hard disk and electrically stores the programs therein when the analyzer 1 performs the process. Thus, the storage unit 46 stores various types of information including the analysis result and the like of the specimen. The storage unit 46 may include a sub-storage apparatus which can read out information stored in a storage medium such as a CD-ROM, a DVD-ROM, and a PC card.

The output unit 47 includes a display, a printer, speakers, and the like, and outputs various types of information related to the analysis under the control of the process control unit 42. The transceiving unit 48 functions as an interface which transceives information in a predetermined format via a communication network (not shown).

Figure 2:
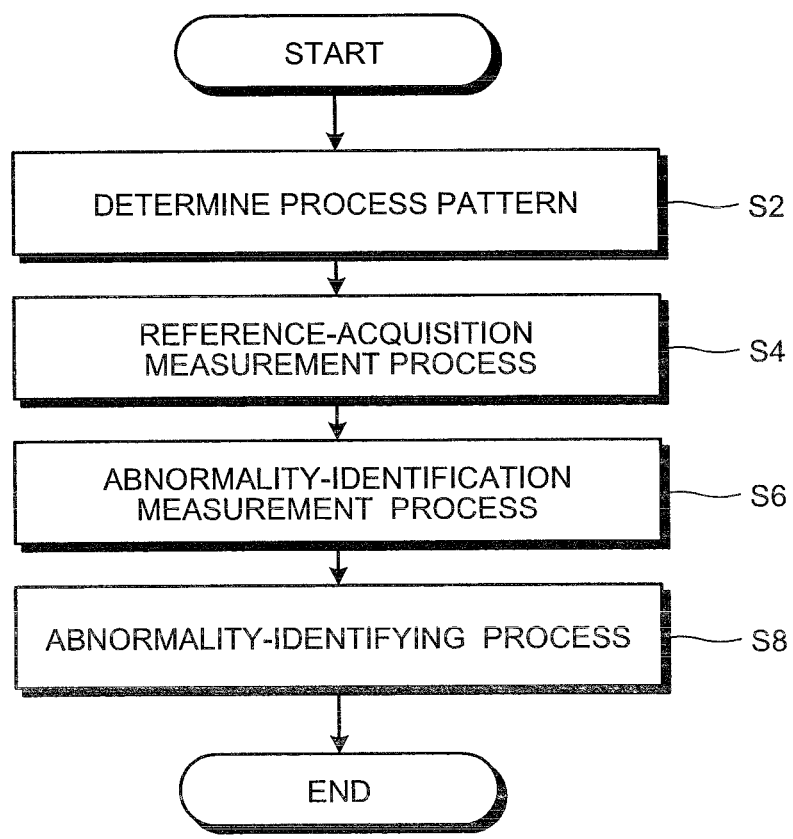
FIG. 2 is a flowchart of a process procedure of an abnormality-identifying process in the analyzer illustrated in FIG. 1.

A procedure of the abnormality-identifying process of the analyzer 1 is described with reference to FIG. 2. As shown in FIG. 2, the input unit 43, being operated by an operator, inputs instruction information to the control unit 41 to identify the removal defect in the first BF cleaning process, the second BF cleaning process, or both. Based on the instruction information input from the input unit 43, the control unit 41 determines a process pattern corresponding to the BF cleaning process for which the presence/absence of the removal defect is to be identified (step S2). Each of the systems included in the measurement system 2 performs a reference-acquisition measurement process under the control of the process control unit 42 (step S4). The reference-acquisition measurement process acquires the reference value, i.e., a measurement result obtained using a low-concentration reagent containing antigens in very low concentrations. Each of the systems included in the measurement system 2 then performs an abnormality-identification measurement process under the control of the process control unit 42 (step S6). The abnormality-identification measurement process acquires the abnormality-identification measurement value, i.e., a measurement result obtained using a high-concentration reagent containing antigens in high concentrations. The identifying unit 45 then performs an abnormality-identifying process (step S8). The abnormality-identifying process determines whether there is a removal defect in the BF cleaning process based on determination on whether the abnormality-identification measurement value acquired in the abnormality-identification measurement process is within an acceptable range set based on the reference value acquired in the reference-acquisition measurement process.

Figure 3:
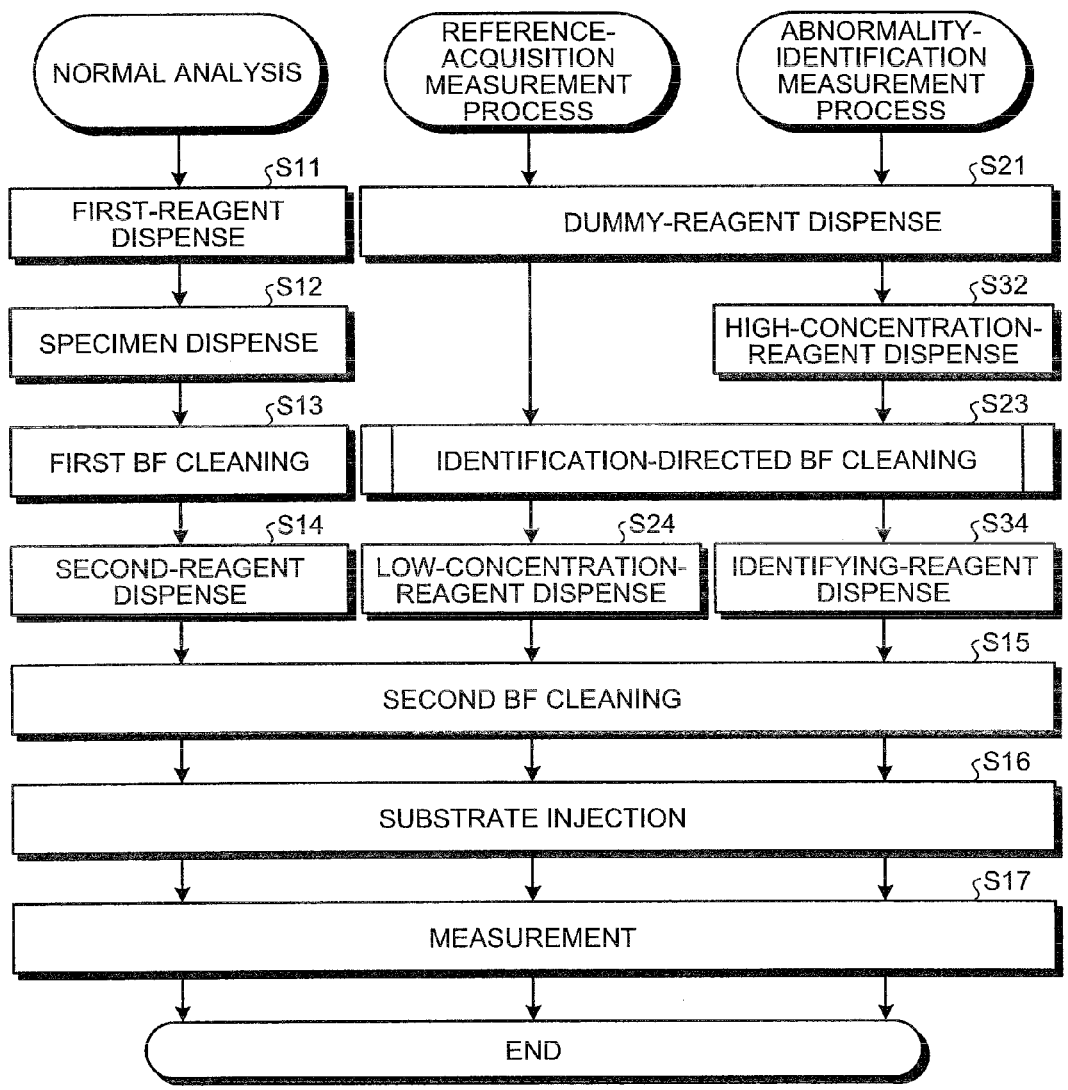
FIG. 3 is a flowchart of a process procedure of a reference-acquisition measurement process and an abnormality-identification measurement process illustrated in FIG. 2.
Figure 4:
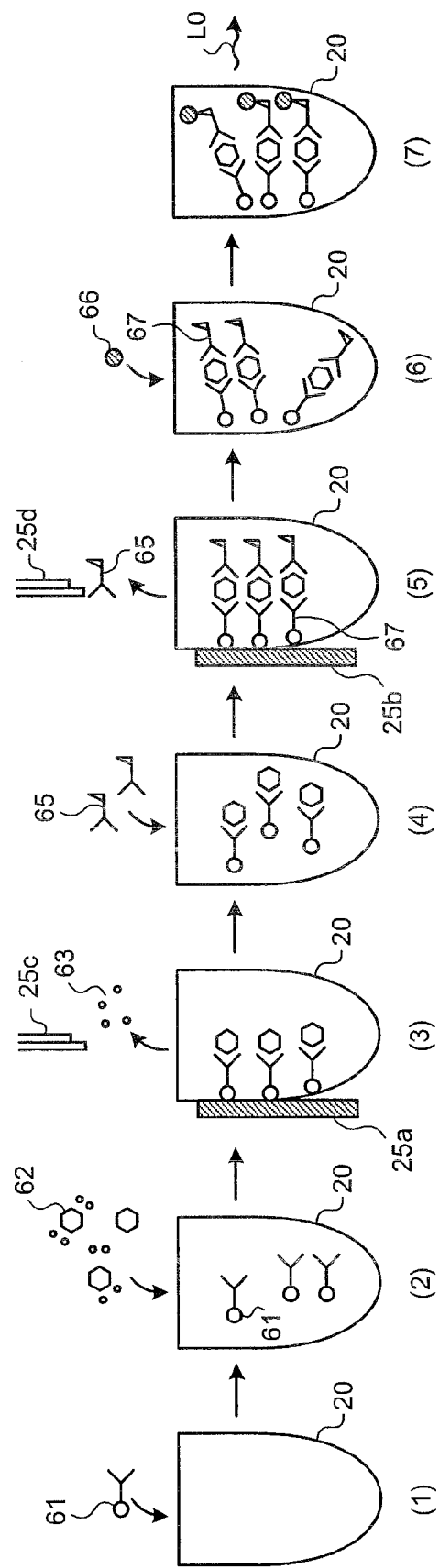
FIG. 4 is a diagram for explaining a normal analysis shown in FIG. 3.

The reference-acquisition measurement process and the abnormality-identification measurement process shown in FIG. 2 are further described with reference to FIGS. 3 to 7. FIG. 3 is a flowchart of process procedures of the reference-acquisition measurement process and the abnormality-identification measurement process shown in FIG. 2. FIG. 3 additionally shows a normal analysis which is normally performed on the specimen along with the reference-acquisition measurement process and the abnormality-identification measurement process. FIG. 4 is a diagram for explaining the normal analysis shown in FIG. 3.

The normal analysis is described. As shown in FIG. 3 and a portion (1) of FIG. 4, in the normal analysis, a cuvette 20 is transferred by the first-cuvette transfer system 32 from a cuvette supply unit not shown in FIG. 1 to a predetermined position on the BF table 25, where a first-reagent dispense process is performed, i.e., where the first reagent containing magnetic particles 61 is dispensed into the cuvette 20 by the first-reagent dispense/transfer system 28 (step S11). After that, as shown in (2) of FIG. 4, a specimen dispense process is performed; i.e., a specimen containing an antigen 62 is dispensed into the cuvette 20 on the BF table 25 in a manner such that the specimen dispense/transfer system 23, onto which the chip supplied from the chip holder 22 is mounted, sucks the specimen 62 out of the specimen vessel 21*a* which has been transferred to the predetermined position by the specimen transfer unit 21 to dispense the specimen 62 into the cuvette 20 (step S12). The liquid in the cuvette 20 is stirred by the stir system on the BF table 25, and then transferred to a middle circular line 24*b* on the immune reaction table 24 by the first-cuvette transfer system 32. In this case, the magnetic particles 61 and antigens 62 in the specimen are bound together in certain reaction time, and thus magnetic-particle carriers are generated.

The cuvette 20 is transferred to the BF table 25 by the first-cuvette transfer system 32. As shown in (3) of FIG. 4, the magnetic-particle carriers are collected by a magnetic collection system 25*a* on the BF table 25, and the BF separation is carried out by the BF cleaning nozzle 25*c* (step S13). As a result, as shown in (3) of FIG. 4, unreacted substances 63 are removed out of the cuvette 20.

As shown in (4) of FIG. 4, after the BF separation, a second-reagent dispense process, which dispenses the second reagent into the cuvette 20 by the second-reagent dispense/transfer system 29, is performed and then the liquid in the cuvette 20 is stirred by the stir system (step S14). The second reagent is a labeled reagent containing a labeled antibody 65. As a result, the magnetic-particle carriers and the labeled antibodies 65 are bound to thereby generate immune complexes 67. Then, the cuvette 20 is transferred to the inner circular line 24*c* on the immune reaction table 24 by the first-cuvette transfer system 32. After certain reaction time, the cuvette 20 is transferred to the BF table 25.

As shown in (5) of FIG. 4, the second BF cleaning process, in which the magnetic-particle carriers are collected by the magnetic collection system 25*b* and the BF separation is performed by the BF cleaning nozzle 25*d*, is performed on the cuvette 20 (step S15). As a result, as shown in (5) of FIG. 4, the labeled antibody 65 which is not bound with the magnetic-particle carrier is removed out of the cuvette 20.

A substrate injection process, which dispenses the substrate solution containing a substrate 66 into the cuvette 20 and stirs the liquid in the cuvette 20, is performed (step S16) as illustrated in (6) of FIG. 4. Then, the cuvette 20 is transferred by the first-cuvette transfer system 32 to an enzyme reaction table 30. After certain reaction time which is needed for the enzyme reaction, the cuvette 20 is transferred by the second-cuvette transfer system 33 to the photometry system 31. As the substrate 66 is bound with the immune complex 67 through the enzyme reaction, light L is emitted from the immune complex 67 as illustrated in (7) of FIG. 4. Then, a measurement process, which measures the light L emitted from the cuvette 20 by the photometry system 31, is performed (step S17). In the normal analysis, in order to detect how much antigen to be analyzed is included in the specimen, after the antigen is bound with the magnetic particles, the labeled antibody is bound with the magnetic-particle carrier to generate the immune complex. The immune complex is reacted with the substrate to generate light. The analysis unit 44 obtains the amount of the antigen by measuring the amount of the generated light.

As described, the normal analysis process, which is performed on the specimen, involves the first-reagent dispense process (step S11), the specimen dispense process (step S12), the first BF cleaning process (step S13), the second-reagent dispense process (step S14), the second BF cleaning process (step S15), the substrate injection process (step S16), and the measurement process (step S17).

Figure 5:
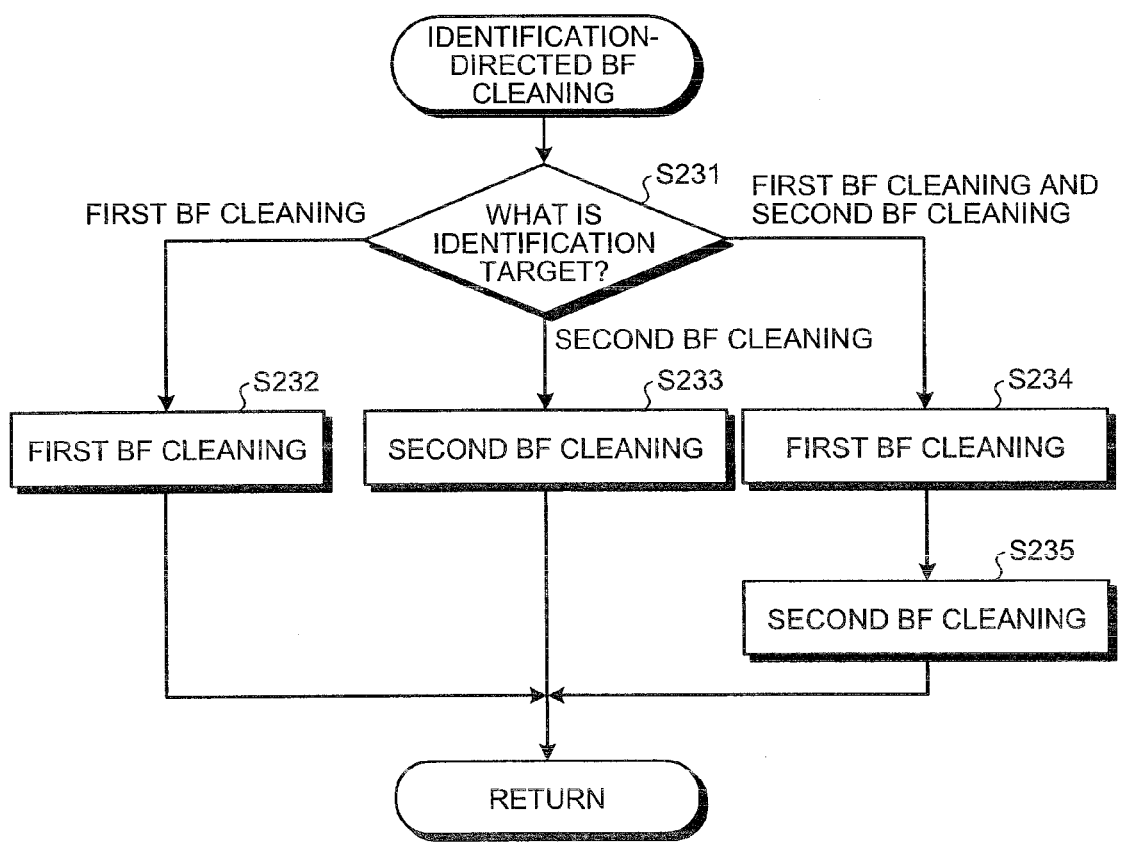
FIG. 5 is a flowchart of a process procedure of an identification-directed BF cleaning process shown in FIG. 3.
Figure 6:
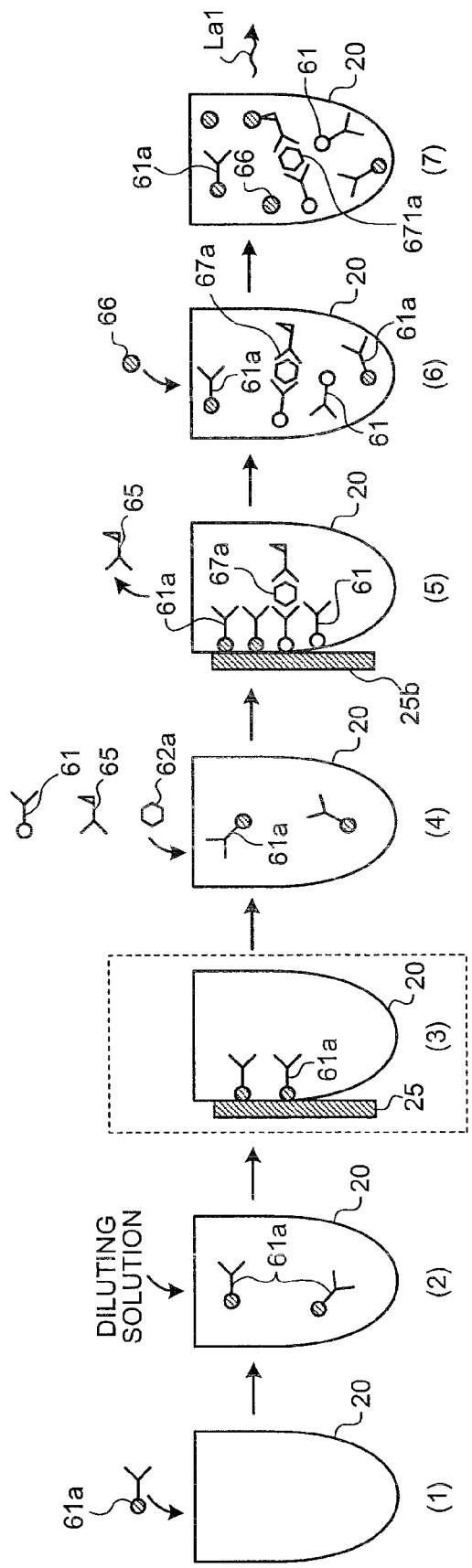
FIG. 6 is an explanatory diagram of the reference-acquisition measurement process shown in FIG. 3.

The reference-acquisition measurement process is described with reference to FIGS. 3, 5, and 6. FIG. 5 is a flowchart of process procedure of the identification-directed BF cleaning process shown in FIG. 3. FIG. 6 is a diagram for explaining the reference-acquisition measurement process shown in FIG. 3.

As shown in FIG. 3 and (1) of FIG. 6, the reference-acquisition measurement process performs a dummy-reagent dispense process (step S21) in place of the first-reagent dispense process in the normal analysis. The dummy-reagent dispense process dispenses a dummy reagent containing a magnetic particle 61a which does not react with the antigen contained in the low-concentration reagent and the high-concentration reagent. The reference-acquisition measurement process then injects a diluting solution to prevent the drying of the magnetic particle 61a which is dispensed in the dummy-reagent dispense process as illustrated in (2) of FIG. 6, without performing the specimen dispense process (step S12) of the normal analysis.

The reference-acquisition measurement process performs the identification-directed BF cleaning process (step S23) as illustrated in (3) of FIG. 6. The identification-directed BF cleaning process performs the BF cleaning process, for which the removal defect is to be identified, following the process pattern determined by the control unit 41. As shown in FIG. 5, in the identification-directed BF cleaning process, the process control unit 42 determines whether the target of identification is the first BF cleaning process, the second BF cleaning process, or both the first BF cleaning process and the second BF cleaning process (step S231). On determining that the first BF cleaning process is to be examined (step S231: first BF cleaning), the process control unit 42 controls each of the systems of the measurement system 2 to perform the first BF cleaning process using the magnetic collection system 25a and the BF cleaning nozzle 25c (step S232). On determining that the second BF cleaning process is to be examined (step S231: second BF cleaning), the process control unit 42 controls each of the systems of the measurement system 2 to perform the second BF cleaning process using the magnetic collection system 25b and the BF cleaning nozzle 25d (step S233). On determining that both the first BF cleaning process and the second BF cleaning process are to be examined (step S231: first BF cleaning and second BF cleaning), the process control unit 42 controls each of the systems of the measurement system 2 to perform the first BF cleaning process (step S234) and subsequently the second BF cleaning process (step S235).

The reference-acquisition measurement process then performs a low-concentration-reagent dispense process (step S24). The low-concentration-reagent dispense process dispenses a labeled antibody 65, a low-concentration reagent containing the antigens 62a of, for example, 0.3 ppm, and the magnetic particle 61 which can react with the antigen 62a in the low-concentration reagent as illustrated in (4) of FIG. 6.

Even when the reagent contains the antigen 62a of 0.3 ppm, the analyzer 1 can output clinically sufficient measurement result of other analyzed antigens. Therefore, the reference-acquisition measurement process performs an analysis process, after dispensing the low-concentration reagent, to allow the light emission of the antigen 62a in the low-concentration reagent, and measures the light-emission amount to acquire the light-emission amount corresponding to the antigen 62a of 0.3 ppm as the reference value. Specifically, the reference-acquisition measurement process stirs and leaves the contents of the cuvette 20 for a predetermined reaction time after the low-concentration-reagent dispense process. Thus, the magnetic particle 61, the antigen 62a in the low-concentration reagent, and the labeled antibody 65 react with each other to form the immune complex 67a as illustrated in (5) of FIG. 6. Then, the reference-acquisition measurement process performs the second BF cleaning process (step S15) in the same manner as in the normal analysis to remove the labeled antibody 65 which is not bound to the magnetic particle carrier. The immune complex 67a, being magnetically collected by the magnetic collection system of the BF table 25, are not removed out of the cuvette 20.

The reference-acquisition measurement process performs the substrate injection process (step S16) as in the normal analysis. The substrate injection process injects the substrate solution containing the substrate 66 into the cuvette 20 as illustrate in (6) of FIG. 6. The immune complex 67a, in the same manner as the immune complex 67 shown in (6) of FIG. 4, undergoes enzyme reaction to be bound with the substrate 66 to form a bound substance 671a which emits light La1 as illustrated in (7) of FIG. 6. The reference-acquisition measurement process then performs the measurement process (step 17) to measure the light La1 emitted from the bound substance 671a, thereby acquires the light-emission amount serving as the reference value.

Even when the reagent contains the antigens of 0.3 ppm, the analyzer 1 can output clinically sufficient measurement result of other analyzed antigen. Therefore, the light-emission amount of the light La1 measured as the reference value in the measurement process of the reference-acquisition measurement process serves as a standard for determining the concentration of impurities which allows the output of clinically sufficient measurement result by the analyzer 1.

Figure 7:
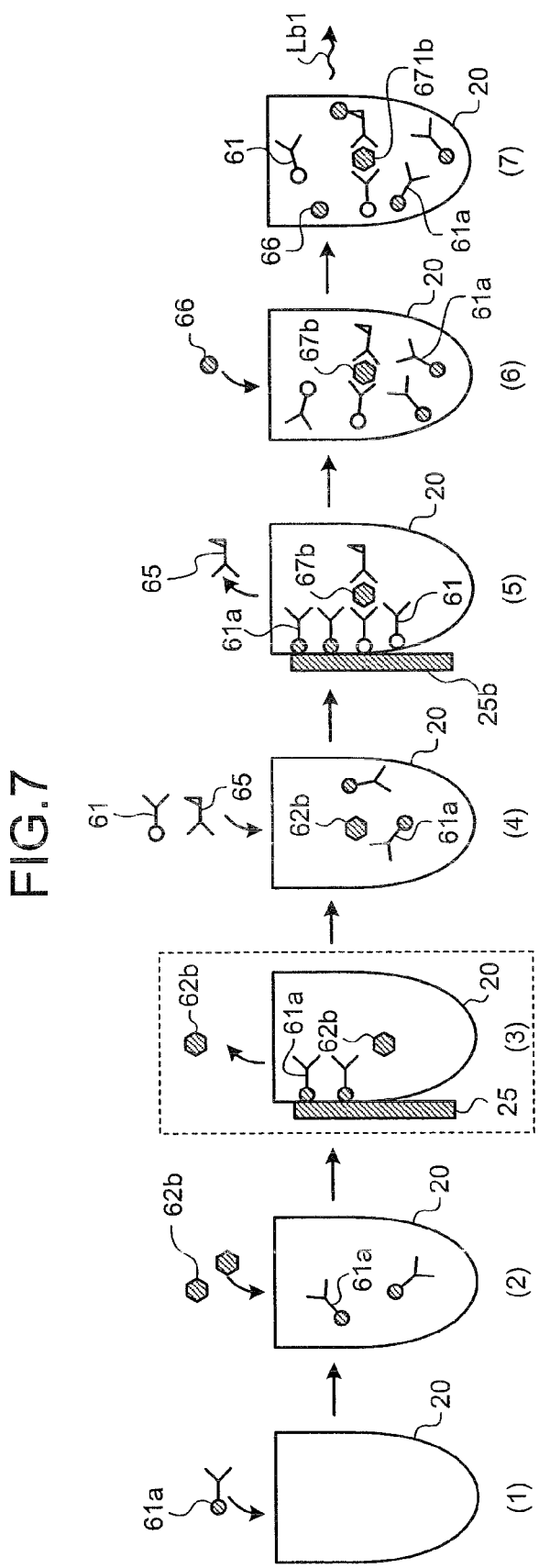
FIG. 7 is an explanatory diagram of the abnormality-identification measurement process shown in FIG. 3.

The abnormality-identification measurement process is described with reference to FIGS. 3 and 7. FIG. 7 is a diagram for explaining the abnormality-identification measurement process shown in FIG. 3. The abnormality-identification measurement process performs the dummy-reagent dispense process (step S21) in the same manner as in the reference-acquisition measurement process as illustrate in FIG. 3 and (1) of FIG. 7. The dummy-reagent dispense process dispenses the dummy reagent containing the magnetic particle 61a.

The abnormality-identification measurement process then performs a high-concentration-reagent dispense process (step S32) in place of the specimen dispense process (step S12) of the normal analysis. The high-concentration-reagent dispense process dispenses the high-concentration reagent containing the antigen 62b in high concentrations into the cuvette 20 as illustrated in (2) of FIG. 7. The high-concentration reagent contains the antigens 62b of, for example, 1 million ppm.

The abnormality-identification measurement process then performs the identification-directed BF cleaning process (step S23) as illustrated in (3) of FIG. 7, in the same manner as the identification-directed BF cleaning process in the reference-acquisition measurement process, following the process procedure shown in FIG. 5. Specifically, when the reference-acquisition measurement process performs the first BF cleaning process as the identification-directed BF cleaning process, the abnormality-identification measurement process performs the first BF cleaning process correspondingly; when the reference-acquisition measurement process performs the second BF cleaning process as the identification-directed BF cleaning process, the abnormality-identification measurement process performs the second BF cleaning process correspondingly; and when the reference-acquisition measurement process performs both the first and the second BF cleaning processes as the identification-directed BF cleaning process, the abnormality-identification measurement process performs both the first and the second BF cleaning processes correspondingly.

When the BF cleaning process is performed properly, the antigen 62b in the high-concentration reagent is removed out of the cuvette 20 and does not remain in the cuvette 20. However, when the BF cleaning nozzle 25c, the BF cleaning nozzle 25d, or both are clogged, for example, the cleaning liquid may not be discharged properly, and/or the liquid and the cleaning liquid in the cuvette 20 may not be sucked out properly. When there is fault in the BF cleaning (i.e., if there is BF cleaning defect) due to clogging of the BF cleaning nozzle and the like, at least a part of the antigen 62b remains in the cuvette 20 as illustrated in (3) of FIG. 7.

To identify the BF cleaning defect, the abnormality-identification measurement process performs the analysis process to allow the antigen 62b remaining in the cuvette 20 to emit light after the identification-directed BF cleaning process, and measures the light-emission amount corresponding to the antigen 62b remaining in the cuvette 20 as the abnormality-identification measurement value. Specifically, the abnormality-identification measurement process performs an identifying-reagent dispense process (step S34). The identifying-reagent dispense process dispenses the identifying reagent, which is a reagent containing the magnetic particle 61 and the labeled antibody 65 as illustrated in (4) of FIG. 7. Thereafter, the contents of the cuvette 20 is stirred and left for a predetermined reaction time. Then, the magnetic particle 61, the remaining antigen 62b, and the labeled antibody 65 are bound with each other to form the immune complex 67b as illustrated in (5) of FIG. 7. The abnormality-identification measurement process then performs the second BF cleaning process (step S15) in the same manner as in the normal analysis to remove the labeled antibody 65 which is not bound to the magnetic particle carrier. The immune complex 67b, being magnetically collected by the magnetic collection system 25b of the BF table 25, are not removed out of the cuvette 20.

The abnormality-identification measurement process performs the substrate injection process (step S16) as in the normal analysis. The substrate injection process injects the substrate solution containing the substrate 66 into the cuvette 20 as illustrated in (6) of FIG. 7. The immune complex 67b, in the same manner as the immune complex 67 shown in (6) of FIG. 4, undergoes enzyme reaction to be bound to the substrate 66 to form a bound substance 671b which emits light Lb1 as illustrated in (7) of FIG. 7. The abnormality-identification measurement process performs the measurement process (step S17) to measure the light Lb1 emitted from the bound substance 671b as the abnormality-identification measurement value. The light-emission amount of the light Lb1 measured as the abnormality-identification measurement value corresponds to the amount of the antigen 62b remaining after the identification-directed BF cleaning process.

The abnormality-identifying process shown in FIG. 2 is described. The identifying unit 45 determines that there is a removal defect in the BF cleaning process performed in the identification-directed BF cleaning process when the abnormality-identification measurement value acquired in the abnormality-identification measurement process is not within an acceptable range set based on the reference value acquired in the reference-acquisition measurement process. The identifying unit 45 performs the abnormality-identifying process referring to a table T1 stored in the storage unit 46 and illustrated in FIG. 8 for a previously-set acceptable range. The reference value acquired in the reference-acquisition measurement process is the light-emission amount of the light La1 measured when the antigen 62a of 0.3 ppm is contained, and serves as a standard for determining the light-emission amount of impurities whose concentration does not obstruct an output of clinically sufficient measurement result of analyzed antigen(s). The table T1 shows standards for determination based on each reference value corresponding to each type of the identification-directed BF cleaning process.

Following describes the abnormality-identifying process performed when the reference-acquisition measurement process and the abnormality-identification measurement process perform the first BF cleaning process as the identification-directed BF cleaning process. When the first BF cleaning process is performed as the identification-directed BF cleaning process, as far as the abnormality-identification measurement value is less than 1.1 time the reference value, i.e., the light-emission amount corresponding to the antigen 62a of 0.3 ppm, the clinically sufficient measurement result can be output for analyzed antigen. When the abnormality-identification measurement value is less than 1.1 times the reference value, the first BF cleaning process is expected to be capable of removing the antigen 62b in the high-concentration reagent to a clinically sufficient level. Therefore, the identifying unit 45 determines that there is no removal defect attributable to the clogging of the BF cleaning nozzle and the like. On the other hand, when the abnormality-identification measurement value is equal to or higher than 1.1 times the reference value, the identifying unit 45 determines that the first BF cleaning process is incapable of removing the antigen 62b in the high-concentration reagent sufficiently and the remaining antigen 62b can affect the measurement result. Thus, the identifying unit 45 determines that there is a removal defect caused by the clogging of the BF cleaning nozzle 25c and the like as illustrated in a field R1 of Table T1.

When the reference-acquisition measurement process and the abnormality-identification measurement process perform the second BF cleaning process as the identification-directed BF cleaning process, and if the abnormality-identification measurement value is less than 1.1 times the reference value, the analyzer 1 can output clinically sufficient measurement result for analyzed antigen. Hence, when the abnormality-identification measurement value is less than 1.1 times the reference value, the identifying unit 45 determines that there is no removal defect in the second BF cleaning process caused by the clogging of the BF cleaning nozzle and the like. On the other hand, when the abnormality-identification measurement value is equal to or higher than 1.1 times the reference value, the identifying unit 45 determines that the second BF cleaning process is incapable of removing the antigen 62b in the high-concentration reagent sufficiently and the remaining antigen 62b can clinically affect the measurement result. Thus, the identifying unit 45 determines that there is a removal defect caused by the clogging of the BF cleaning nozzle 25d and the like as illustrated in a field R2 of Table T1.

When the reference-acquisition measurement process and the abnormality-identification measurement process perform both the first and the second BF cleaning processes as the identification-directed BF cleaning process, and if the abnormality-identification measurement value is less than 1.2 times the reference value, the analyzer 1 can output clinically sufficient measurement result for analyzed antigen. Hence, when the abnormality-identification measurement value is less than 1.2 times the reference value, the identifying unit 45 determines that there is no removal defect in the first and the second BF cleaning processes caused by the clogging of the BF cleaning nozzle and the like. On the other hand, when the abnormality-identification measurement value is equal to or higher than 1.2 times the reference value, the identifying unit 45 determines that the first BF cleaning process, the second BF cleaning process, or both are incapable of removing the antigen 62b in the high-concentration reagent sufficiently and the remaining antigen 62b can clinically affect the measurement result. Thus, the identifying unit 45 determines that there is a removal defect caused by the clogging of the BF cleaning nozzles 25c, 25d and the like as illustrated in a field R3 of Table T1.

The analyzer 1 according to the first embodiment determines whether the BF cleaning process removes the contents of the cuvette to a clinically sufficient level based on the reference value, i.e., the light-emission amount corresponding to the concentration of impurities which allows the output of clinically sufficient measurement result, and the abnormality-identification measurement value, i.e., the light-emission amount after the BF cleaning process is actually performed on the high-concentration reagent. According to the first embodiment, the reference-acquisition measurement process and the abnormality-identification measurement process perform processes other than the BF cleaning process, for which the abnormality is to be identified, substantially in the same manner. Therefore, the contribution of other processes to the abnormality does not need to be considered, and the removal defect of the BF cleaning process can be examined correctly. Further, according to the first embodiment, the presence/absence of the abnormality in the BF cleaning process can be identified based on the measurement result obtained by the photometry system 31. Therefore, an independent spectrophotometer for calorimetric measurement is not required to be provided apart from the analyzer itself, unlike the conventional technology. Thus, according to the first embodiment, the abnormality of the analyzer can be identified correctly and easily.

The first embodiment is a case where the employed low-concentration reagent and the high-concentration reagent which contain as their component, the antigen reacting with the magnetic particle 61, in the same manner as the antigen contained in actual specimen such as blood and urine. However, this example should not be taken as limiting. For example, the low-concentration reagent and the high-concentration reagent may contain as their component, a labeled substance which reacts with the substrate (enzyme) acting as a light-emitting substrate. In this case, the analyzer 1 performs the reference-acquisition measurement process using a reagent which contains labeled substances in predetermined very low concentrations as the low-concentration reagent. Further, the analyzer 1 performs the abnormality-identification measurement process using a reagent which contains labeled substances in predetermined high concentrations as the high-concentration reagent.

Figure 9:
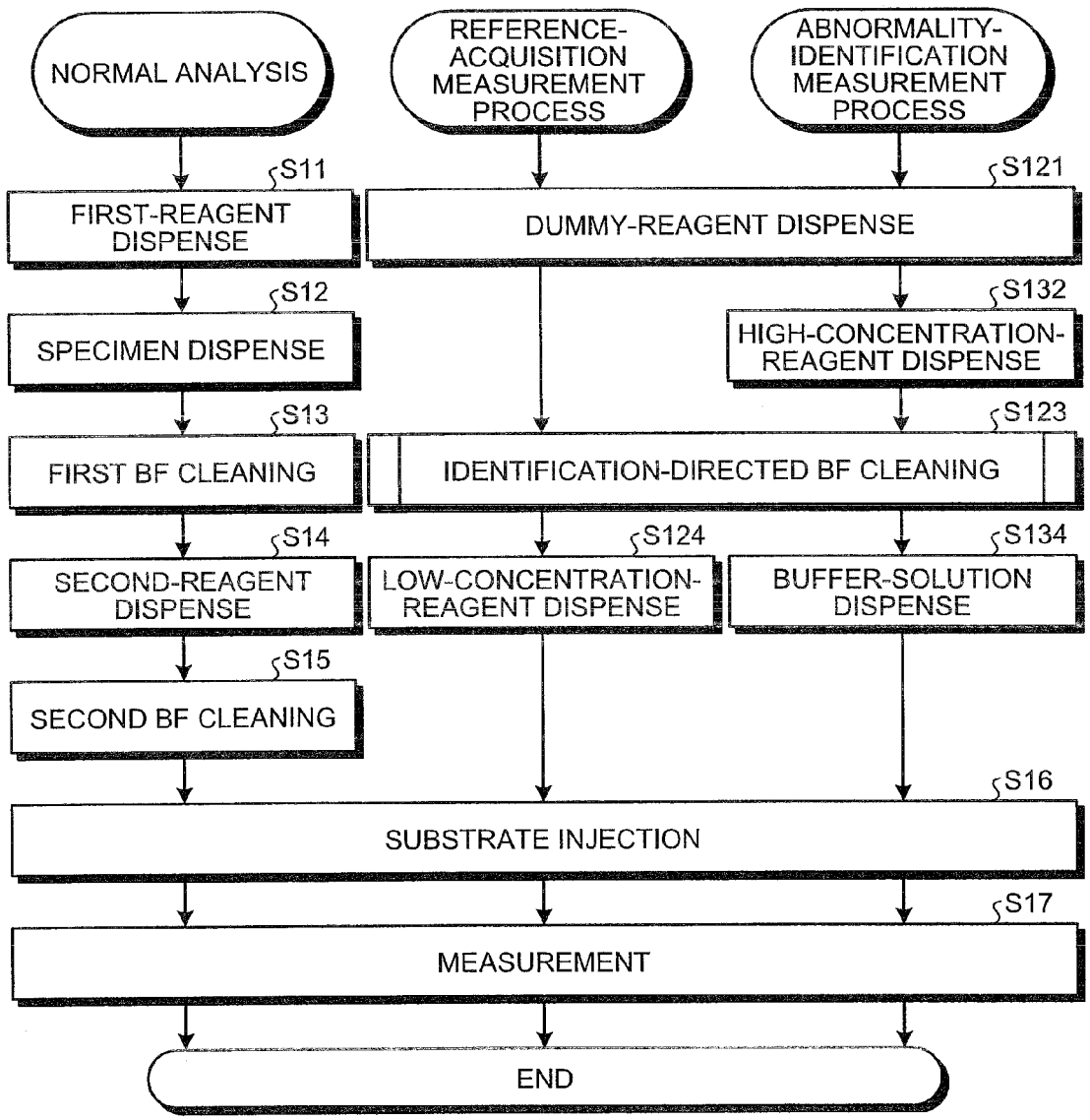
FIG. 9 is a flowchart of another example of process procedures of the reference-acquisition measurement process and the abnormality-identification measurement process.
Figure 10:
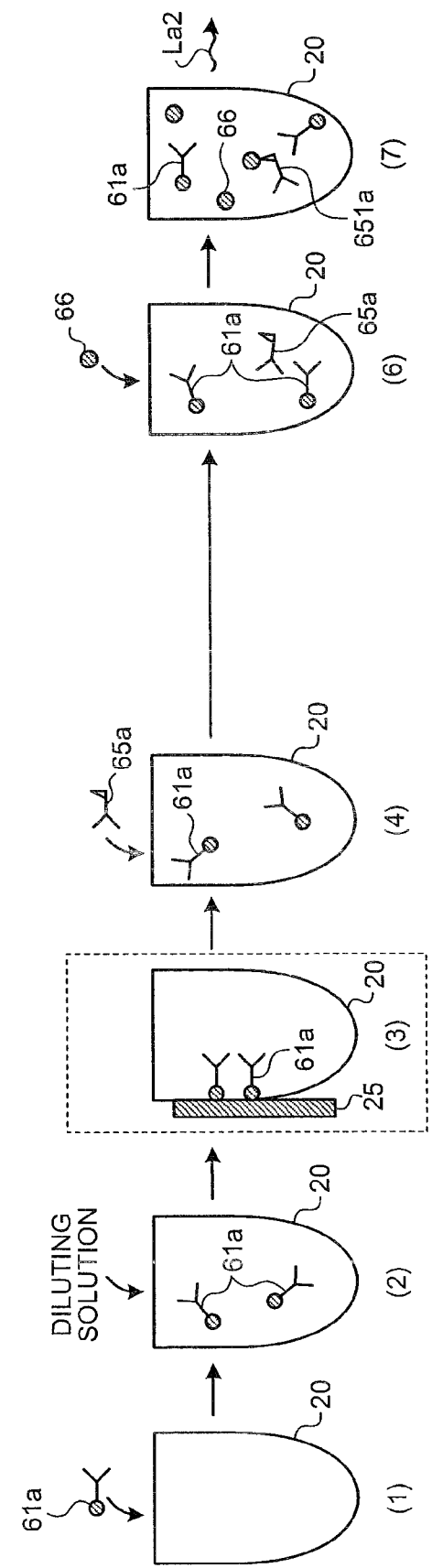
FIG. 10 is an explanatory diagram of the reference-acquisition measurement process shown in FIG. 9.

Following describes a case where the low-concentration reagent containing the labeled substance as a component is employed in the reference-acquisition measurement process shown in FIG. 2, with reference to FIGS. 9 and 10. The reference-acquisition measurement process performs the dummy-reagent dispense process (step S121) for dispensing the dummy reagent containing the magnetic particle 61a, and after the injection of diluting solution, performs the identification-directed BF cleaning process (step S123) as illustrated in FIG. 9 and (1) to (3) of FIG. 10, in the same manner as the case illustrated in FIG. 3 and (1) to (3) of FIG. 6. Then, the reference-acquisition measurement process performs the low-concentration-reagent dispense process (step S124) to dispense the low-concentration reagent containing the labeled antibody 65a of 0.3 ppm into the buffer solution as illustrate in (4) of FIG. 10. The labeled antibody 65a and the substrate 66 undergo enzyme reaction to be bound with each other and emit light. To acquire the light-emission amount corresponding to the labeled antibody 65a of 0.3 ppm as the reference value, the substrate injection process (S16) is first performed, in which the substrate solution containing the substrate 66 is injected into the cuvette 20 as illustrated in FIG. 9 and (6) of FIG. 10. After the substrate 66 and the labeled antibody 65a undergo predetermined enzyme reaction to form a bound substance 651a which emits light La2, the analyzer 1 performs the measurement process (step S17) to measure the light La2, to thereby acquire the light-emission amount as the reference value.

As shown in FIGS. 9 and 10, when the employed low-concentration reagent contains the labeled antibody 65a, which is bound to the substrate 66 acting as a light-emitting substrate, as a component, the analyzer 1 can acquire the light-emission amount as the reference value only through the enzyme reaction between the labeled antibody 65a and the substrate 66. In other words, when the low-concentration reagent contains the labeled antibody 65a as the component, the analyzer 1 does not need to perform processes required when the low-concentration reagent contains the antigen 62a to make the antigen 62a emit light. These processes include the process for injecting the magnetic particle 61 and the labeled antibody 65 as illustrated in (4) of FIG. 6, and the second BF cleaning process (step S15) for removing the labeled antibody 65 which is not bound to the magnetic particle carrier.

Figure 11:
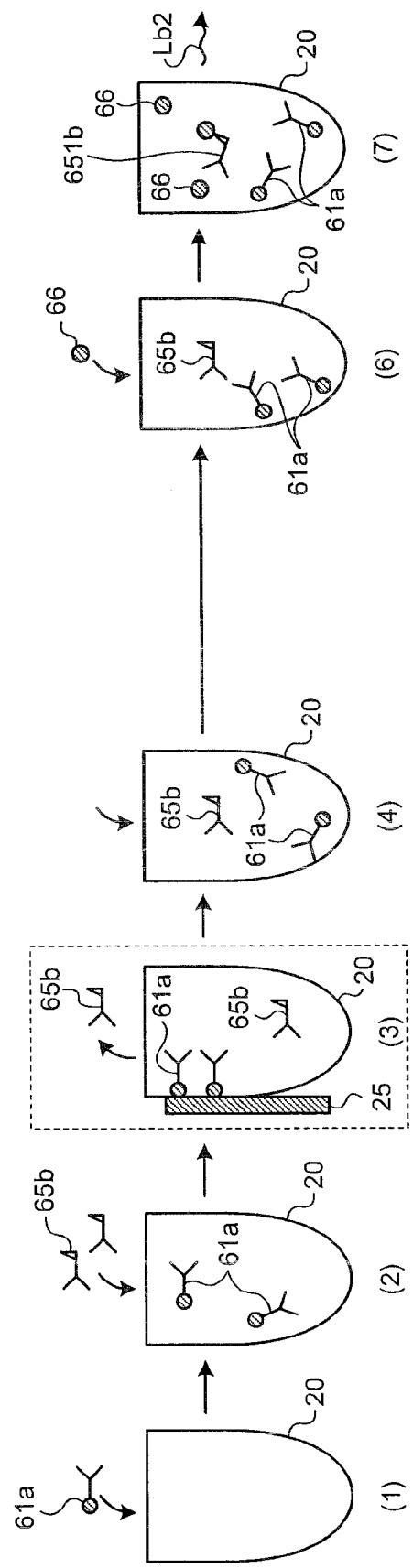
FIG. 11 is an explanatory diagram of the abnormality-identification measurement process shown in FIG. 9.

Following describes, referring to FIGS. 9 and 11, a case where the high-concentration reagent containing the labeled substance as a component is employed in the abnormality-identification measurement process shown in FIG. 2. The abnormality-identification measurement process performs the dummy-reagent dispense process (step S121) to dispense the dummy reagent containing the magnetic particle 61a as illustrate in FIG. 9 and (1) of FIG. 11, in the same manner as illustrated in FIG. 3 and (1) of FIG. 7. Then, the abnormality-identification measurement process proceeds to the high-concentration-reagent dispense process (step S132) to dispense the high-concentration reagent containing the labeled antibody 65b of, for example, 1 million ppm into the cuvette 20 as illustrated in FIG. 9 and (2) of FIG. 11. After the injection of the diluting solution, the identification-directed BF cleaning process (step S123) is performed as illustrated in FIG. 9 and (3) of FIG. 11. The labeled antibody 65b does not have magnetism. Therefore, if the BF cleaning process is not defective, all the labeled antibodies 65b are removed in the identification-directed BF cleaning process. On the other hand, when there is a BF cleaning defect, the labeled antibody 65b is left in the cuvette 20. To confirm presence/absence of the abnormality in the BF cleaning process, the light emission amount corresponding to the labeled antibody 65 remaining in the cuvette 20 is measured as the abnormality-identification measurement value. Specifically, a buffer-solution dispense process (step S134) is performed to make the condition the same as that in the low-concentration-reagent dispense process in the reference-acquisition measurement process. The buffer-solution dispense process dispenses the buffer solution alone as illustrated in (4) of FIG. 11. Then, the substrate injection process (step S16) is performed as illustrated in FIG. 9 and (6) of FIG. 11 to inject the substrate solution containing the substrate 66 into the cuvette 20. After predetermined enzyme reaction, the substrate 66 and the labeled antibody 65b remaining in the cuvette 20 are bound to form a bound substance 651b which emits light Lb2. The analyzer 1 performs the measurement process (step S17) to measure the light Lb2 to thereby acquire the light-emission amount as the abnormality-identification measurement value.

When the high-concentration reagent contains as its component, the labeled antibody 65b which is bound to the substrate 66 acting as the light-emitting substrate, the analyzer 1 can acquire the light-emission amount serving as the abnormality-identification measurement value only through the enzyme reaction between the labeled antibody 65b and the substrate 66. In other words, the analyzer 1 does not need to perform processes required when the high-concentration reagent contains the antigen 62b to make the antigen 62b remaining in the cuvette 20 emit light. These processes include the process for injecting the magnetic particle 61 and the labeled antibody 65 as illustrated in (4) of FIG. 7, and the second BF cleaning process (step S15) for removing the labeled antibody 65 which is not bound to the magnetic particle carrier.

The analyzer 1 identifies the abnormality in each of the BF cleaning processes performed in the identification-directed BF cleaning process by referring to the table T1 illustrated in FIG. 8 and comparing the reference value acquired as illustrated in (7) of FIG. 10 and the abnormality-identification measurement value acquired as illustrated in (7) of FIG. 11.

By employing the low-concentration reagent and the high-concentration reagent containing the labeled substance as their component, the analyzer 1 can eliminate the second BF cleaning process shown in FIG. 3, (5) of FIG. 6, and (5) of FIG. 7 in the reference-acquisition measurement process and the abnormality-identification measurement process, whereby the analyzer 1 can identify the abnormality in the BF cleaning process more promptly.

When the second BF cleaning process is performed in addition to the identification-directed BF cleaning process as illustrated in FIGS. 3, 6, and 7, and if there is an abnormality in the performance of the BF cleaning process to remove unreacted substances, not only that the abnormality-identification measurement process cannot measure the remaining amount of the high-concentration reagent correctly, but that the reference-acquisition measurement process may not be able to measure the reference value correctly. However, when the employed low-concentration reagent and high-concentration reagent contain the labeled antibodies as the component as illustrated in FIGS. 9, 10, and 11, the analyzer 1 does not need to perform the BF cleaning process other than the identification-directed BF cleaning process. Therefore, even if there is an abnormality in the performance of BF cleaning process to remove unreacted substances, the reference value and the abnormality-identification measurement value can be acquired without negative influence therefrom, and the abnormality in the BF cleaning process can be identified even more correctly.

Further, as the labeled antibody can emit light simply by binding to the substrate (enzyme) as illustrated in FIGS. 9, 10, and 11, the magnetic particle and the labeled antibody which make the antigen emit light are not required when the low-concentration reagent and the high-concentration reagent contain the labeled antibody as their component. Thus, when the low-concentration reagent and the high-concentration reagent contain the labeled antibody as their component, the analyzer 1 does not need to use the reagent containing the magnetic particle and the labeled antibody for identifying the abnormality in the BF cleaning process, whereby the amount of reagent employed in abnormality identification of the BF cleaning process can be reduced.

A second embodiment is described. Described below as the second embodiment is a case where presence/absence of cleaning defect of a dispense system is identified. The dispense system dispenses liquid in analysis processes on a specimen. In the second embodiment, the light-emission amount of the low-concentration reagent is employed as a reference value. After a dispense system dispenses the high-concentration reagent, a cleaning process is performed on the dispense system. Then, a dispense/transfer system dispenses zero-concentration reagent which contains no antigen. Thereafter, if the light-emission amount is equal to or higher than predetermined times the reference value, the analyzer determines that there is a cleaning defect of the dispense system. The analyzer of the second embodiment has the same configuration as that of the analyzer 1 shown in FIG. 1.

Figure 12:
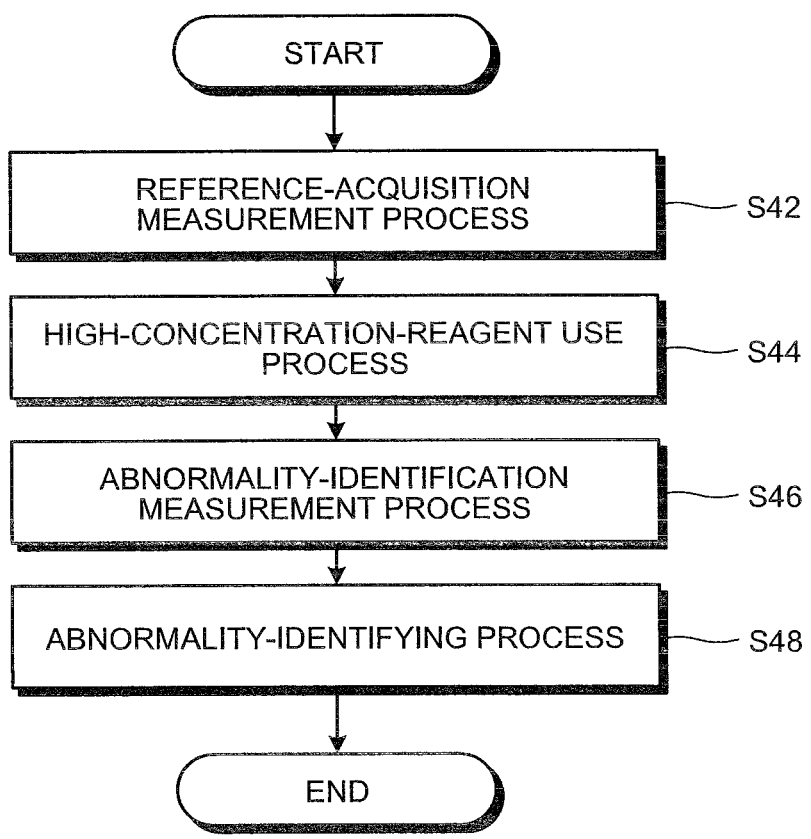
FIG. 12 is a flowchart of a process procedure of an abnormality-identifying process according to a second embodiment.

Process procedure of the abnormality-identifying process according to the second embodiment is described with reference to FIG. 12. As shown in FIG. 12, each of the systems included in the measurement system 2 performs the reference-acquisition measurement process (step S42) under the control of the process control unit 42 to acquire the measurement result obtained using the low-concentration reagent containing antigens in very low concentrations, as a reference value. Then, each of the systems included in the measurement system 2 performs a high-concentration-reagent use process (step S44) to inject the high-concentration reagent containing antigens in high concentrations using a dispense/transfer system for which the cleaning defect is to be identified. Then, each of the systems included in the measurement system 2 performs the abnormality-identification measurement process (step S46) to measure the light-emission amount as the abnormality-identification measurement value, after a cleaned dispense/transfer system dispenses a zero-concentration reagent into a cuvette different from the cuvette in which the high-concentration reagent is dispensed. The identifying unit 45 performs the abnormality-identifying process (step S48) to identify the presence/absence of cleaning defect of the dispense system based on whether the abnormality-identification measurement value acquired in the abnormality-identification measurement process is within an acceptable range set based on the reference value acquired in the reference-acquisition measurement process.

Figure 13:
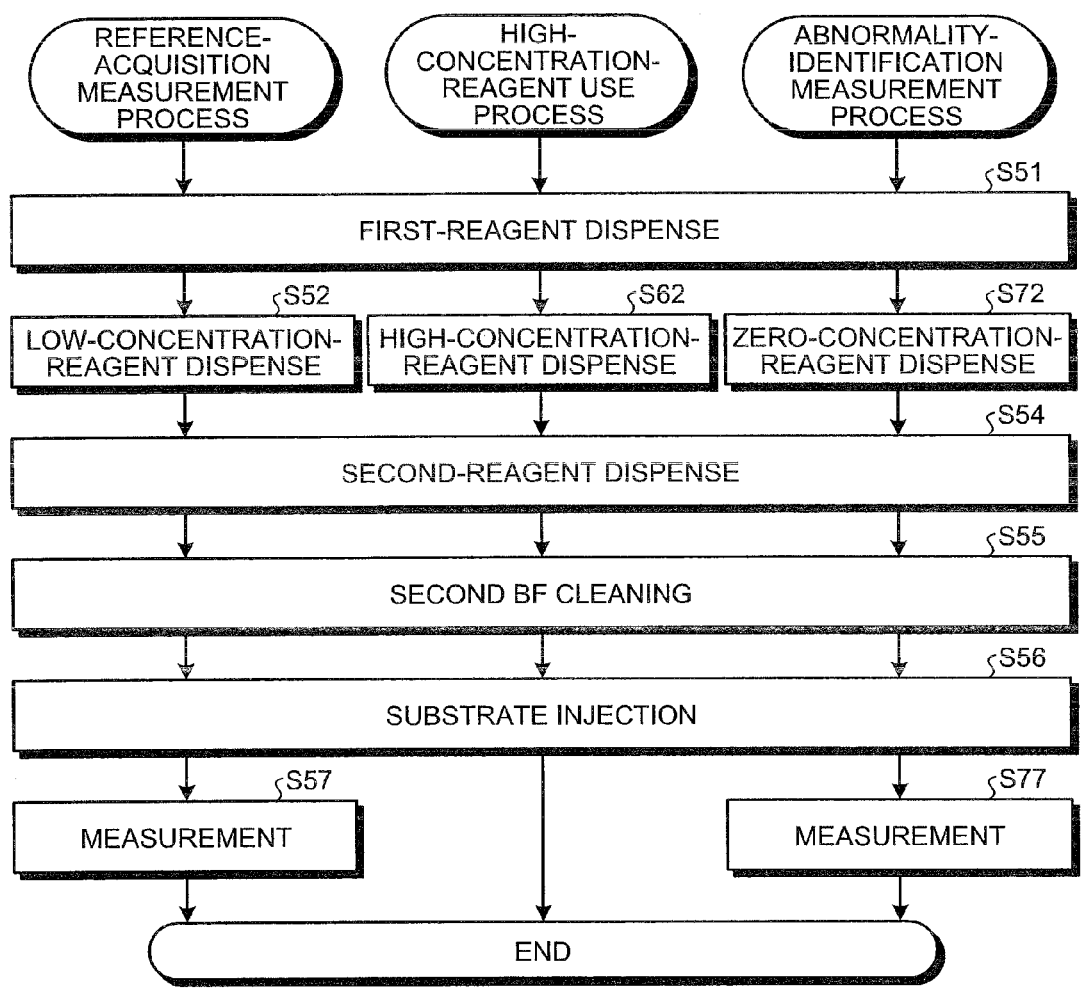
FIG. 13 is a flowchart of a process procedure of a reference-acquisition measurement process, a high-concentration-reagent use process, and an abnormality-identification measurement process illustrated in FIG. 12.
Figure 14:
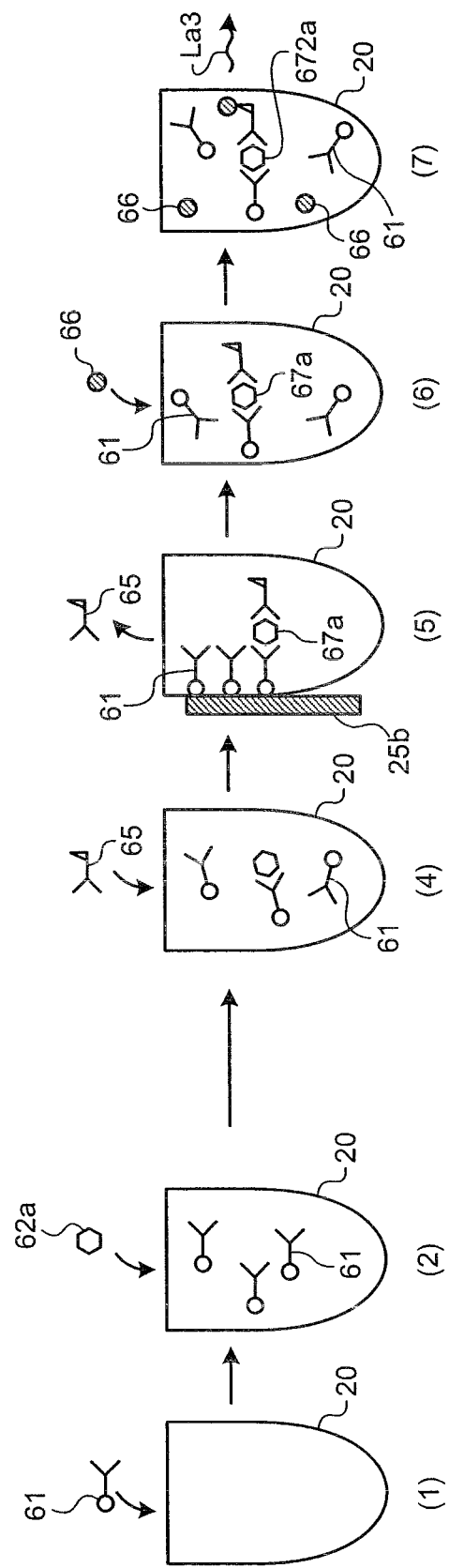
FIG. 14 is an explanatory diagram of the reference-acquisition measurement process shown in FIG. 13.
Figure 15:
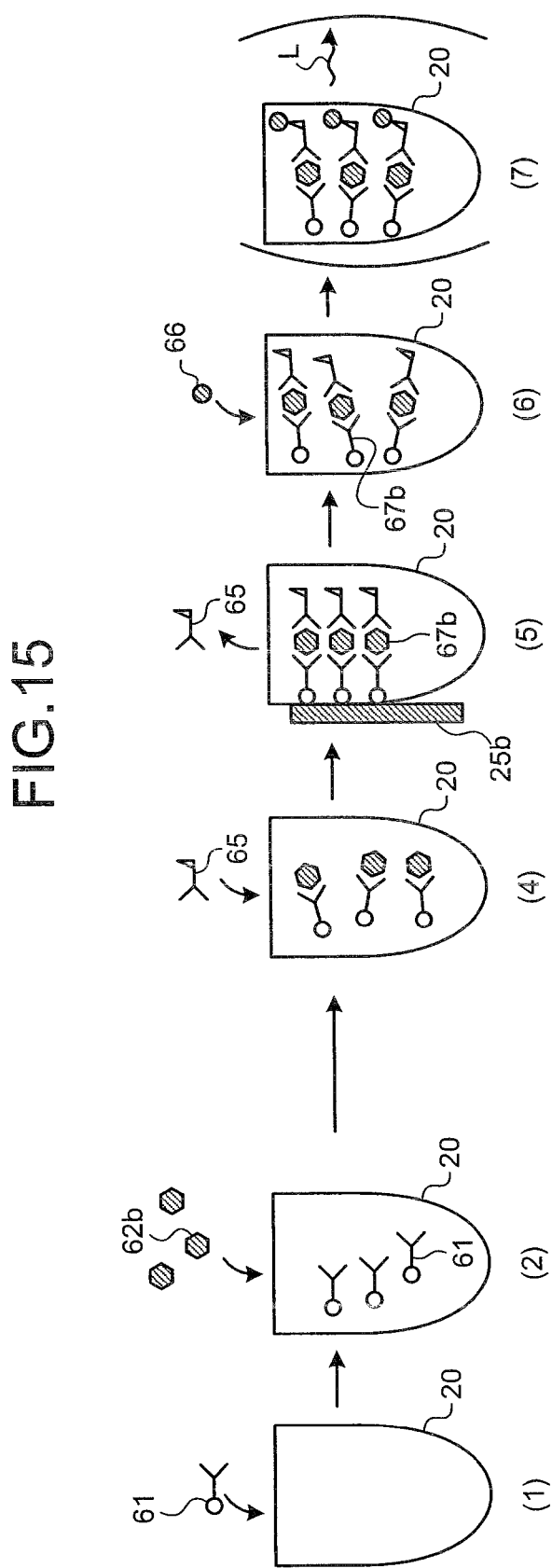
FIG. 15 is an explanatory diagram of the high-concentration-reagent use process shown in FIG. 13.
Figure 16:
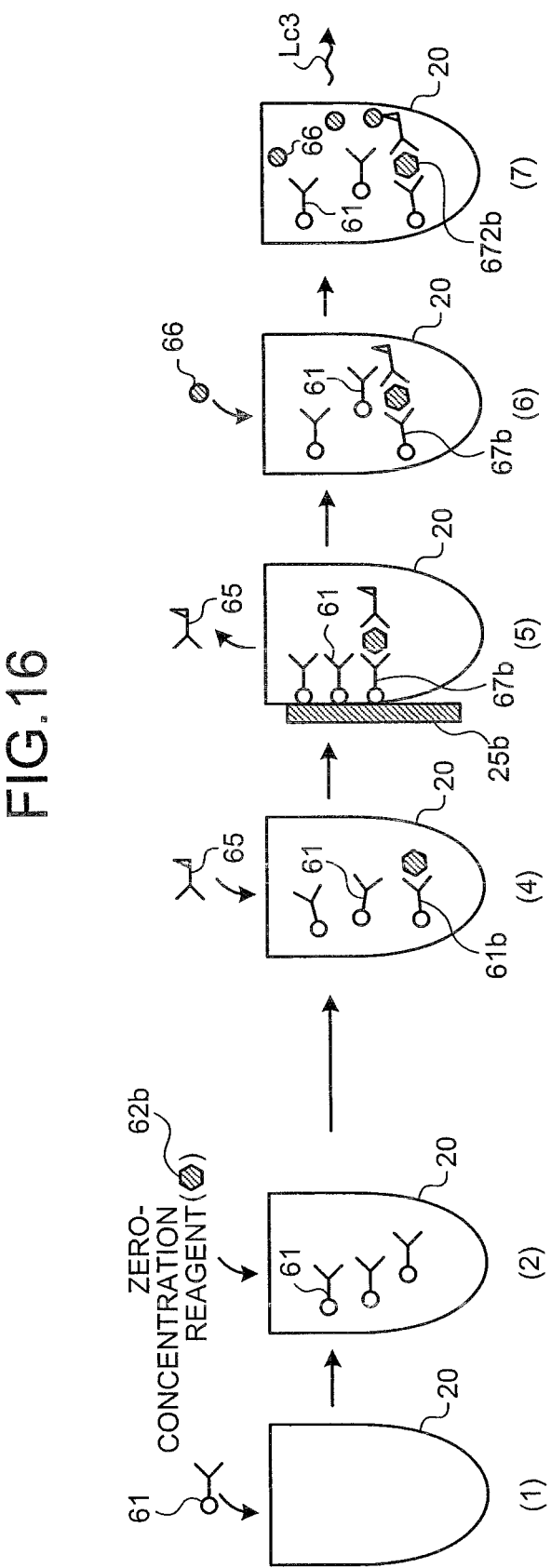
FIG. 16 is an explanatory diagram of the abnormality-identification measurement process shown in FIG. 13.

The reference-acquisition measurement process, the high-concentration-reagent use process, and the abnormality-identification measurement process shown in FIG. 12 are described with reference to FIGS. 13 to 16. FIG. 13 is a flowchart of process procedure of the reference-acquisition measurement process, the high-concentration-reagent use process, and the abnormality-identification measurement process shown in FIG. 12. FIG. 14 is a diagram for explaining the reference-acquisition measurement process shown in FIG. 13, FIG. 15 is a diagram for explaining the high-concentration-reagent use process shown in FIG. 13, and FIG. 16 is a diagram for explaining the abnormality-identification measurement process shown in FIG. 13.

The reference-acquisition measurement process is described. As shown in FIG. 13 and (1) of FIG. 14, the reference-acquisition measurement process performs the first-reagent dispense process (step S51) to dispense a first reagent containing the magnetic particle 61 which can react with an antigen contained in the low-concentration reagent and the high-concentration reagent. Further, the reference-acquisition measurement process performs the low-concentration-reagent dispense process (step S52) to dispense a low-concentration reagent containing the antigen 62a of, for example, 0.3 ppm to the cuvette 20 using a probe of a dispense/transfer system, for which the cleaning defect is to be identified, as illustrated in (2) of FIG. 14. The contents of the cuvette 20 is stirred and left for a predetermined reaction time, and the magnetic particle 61 and the antigen 62a in the low-concentration reagent are bound with each other to form a magnetic particle carrier.

Even when the reagent contains the antigen 62a of 0.3 ppm, the analyzer 1 can output clinically sufficient measurement result of other analyzed antigen. Hence, after dispensing the low-concentration reagent, the reference-acquisition measurement process performs an analysis process to make the antigen 62a in the low-concentration reagent emit light, and measures the light-emission amount to acquire the light-emission amount corresponding to the antigen 62a of 0.3 ppm as the reference value.

Specifically, after the low-concentration-reagent dispense process, the reference-acquisition measurement process performs the second-reagent dispense process (step S54) to dispense the second reagent containing the labeled antibody 65 into the cuvette 20 using the second-reagent dispense/transfer system 29 as illustrated in (4) of FIG. 14. Thereafter, the contents of the cuvette 20 is stirred and left for a predetermined reaction time. Then, the magnetic particle carrier and the labeled antibody 65 are bound with each other to form the immune complex 67a as illustrated in (5) of FIG. 14. Then, the reference-acquisition measurement process performs the second BF cleaning process (step S55) as in the normal analysis to remove the labeled antibody 65 which is not bound to the magnetic particle carrier as illustrated in (5) of FIG. 14. The immune complex 67a, being magnetically collected by the magnetic collection system of the BF table 25, are not removed out of the cuvette 20. The reference-acquisition measurement process then performs the substrate injection process (step S56) to inject the substrate solution containing the substrate 66 to the cuvette 20 as illustrated in (6) of FIG. 14, as in the normal analysis. The immune complex 67a, in the same manner as the immune complex 67 shown in (6) of FIG. 4, undergoes enzyme reaction to be bound to the substrate 66 to form a bound substance 672a which emits light La3 as illustrated in (7) of FIG. 14. The reference-acquisition measurement process then performs the measurement process (step S57) to measure the light La3 emitted from the bound substance 672a, to thereby acquire the light-emission amount as the reference value.

The high-concentration-reagent use process is described with reference to FIGS. 13 and 15. The high-concentration-reagent use process performs the first-reagent dispense process (step S51) to dispense the first reagent containing the magnetic particle 61 as illustrated in FIG. 13 and (1) of FIG. 15 in the same manner as in the reference-acquisition measurement process. Then, the high-concentration-reagent use process performs the high-concentration-reagent dispense process (step S62) to dispense the high-concentration reagent containing the antigen 62b in high concentrations to the cuvette 20 using the probe of a dispense/transfer system, for which the cleaning defect is to be identified, as illustrate in (2) of FIG. 15. The high-concentration reagent contains the antigens 62b of, for example, 1 million ppm. The probe of the dispense/transfer system which dispenses the high-concentration reagent is cleaned before the next liquid dispensing. Thereafter, the high-concentration-reagent use process performs the second-reagent dispense process (step S54), the second BF cleaning process (step S55), and the substrate injection process (step S56) in the same manner as in the reference-acquisition measurement process as illustrated in (4) to (6) of FIG. 15. In the high-concentration-reagent use process, the immune complex 67b is bound to the substrate 66 and emits light L as illustrated in (7) of FIG. 15. However, the high-concentration-reagent use process finishes without measuring the light L.

The abnormality-identification measurement process is described with reference to FIGS. 13 and 16. The abnormality-identification measurement process performs the first-reagent dispense process (step S51) to dispense the first reagent containing the magnetic particle 61 as illustrated in FIG. 13 and (1) of FIG. 16 in the same manner as in the reference-acquisition measurement process and the high-concentration-reagent use process.

Figures 17, 18:
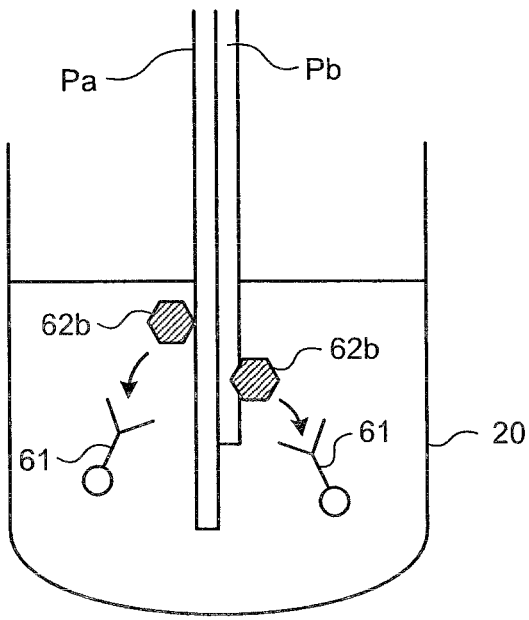
FIG. 17 is an explanatory diagram for explaining antigen incorporation shown in a portion (2) of FIG. 16.
FIG. 18 shows an exemplary table that is used in the abnormality-identifying process shown in FIG. 12.

The abnormality-identification measurement process performs the zero-concentration-reagent dispense process (step S72) to dispense the zero-concentration reagent using the probe of a dispense/transfer system, for which the cleaning defect is to be identified, as illustrated in (2) of FIG. 16. As shown in FIG. 17, when probes Pa and Pb of the dispense/transfer system are not sufficiently cleaned, the antigen 62b in the high-concentration reagent dispensed by the probes Pa and Pb before the zero-concentration reagent is dispensed may not be removed sufficiently, and remain on the probes PA and Pb. If the probes Pa and Pb dispense the zero-concentration reagent while the antigens 62b still remain on the probes Pa and Pb, the antigens 62b remaining on the probes Pa and Pb enter the cuvette 20. To identify such probe-cleaning defect, after the zero-concentration-reagent dispense process, the abnormality-identification measurement process performs the analysis process to make the antigen 62b remaining on the probes Pa and Pb and entering the cuvette 20 emit light, and measures the light emission amount as the abnormality-identification measurement value.

Specifically, after the zero-concentration-reagent dispense process, the contents of the cuvette 20 is stirred and left for a predetermined reaction time so that the magnetic particle 61 and the antigen 62b remaining on the probes Pa and Pb and entering the cuvette 20 are bound with each other to form the magnetic particle carrier 61b. Thereafter the abnormality-identification measurement process performs the second-reagent dispense process (step S54) to dispense the second reagent containing the labeled antibody 65 into the cuvette 20 as illustrated in (4) of FIG. 16. After the contents of the cuvette 20 is stirred and left for a predetermined reaction time, the magnetic particle carrier 61b and the labeled antibody 65 are bound with each other to form the immune complex 67b. Then, the abnormality-identification measurement process performs the second BF cleaning process (step S55) as illustrated in (5) of FIG. 16 in the same manner as in the reference-acquisition measurement process to remove the labeled antibody 65 which is not bound to the magnetic particle carrier 61b. The immune complex 67b, being magnetically collected by the magnetic collection system 25b of the BF table 25, are not removed out of the cuvette 20.

The abnormality-identification measurement process performs the substrate injection process (step S56) to inject the substrate solution containing the substrate 66 into the cuvette 20 as illustrated in (6) of FIG. 16 in the same manner as in the reference-acquisition measurement process. The immune complex 67b, in the same manner as the immune complex 67 shown in (6) of FIG. 4, undergoes enzyme reaction to be bound to the substrate 66 to form a bound substance 672b which emits light Lc3 as illustrated in (7) of FIG. 16. The abnormality-identification measurement process then performs the measurement process (step S77) to measure the light Lc3 emitted from the bound substance 672b thereby to acquire the light-emission amount which is the abnormality-identification measurement value. The light-emission amount of the light Lc3 measured as the abnormality-identification measurement value corresponds to the amount of the antigen 62b which remains on the probe after the probe, for which the cleaning defect is to be identified, is cleaned, and enters the cuvette 20 when the probe dispenses the liquid for the next time.

The abnormality-identifying process shown in FIG. 12 is described. The identifying unit 45 determines that there is a cleaning defect in the probe which dispenses the high-concentration reagent when the abnormality-identification measurement value acquired in the abnormality-identification measurement process is not within an acceptable range set based on the reference value acquired in the reference-acquisition measurement process. The identifying unit 45 performs the abnormality-identifying process by referring to a table T2 stored in the storage unit 46 and illustrated in FIG. 18 for the previously-set acceptable range. The reference value acquired in the reference-acquisition measurement process is the light-emission amount of light La emitted when the antigen 62a of 0.3 ppm is contained, and serves as a standard for determining the light-emission amount of impurities whose concentration allows an output of clinically sufficient measurement results of analyzed antigen(s). The table T2 shows the standard for determination based on the reference value.

When the abnormality-identification measurement value is less than 1.1 times the reference value, i.e., the light-emission amount corresponding to the antigen 62a of 0.3 ppm, the analyzer 1 can output clinically sufficient measurement result of the analyzed antigen. When the abnormality-identification measurement value is less than 1.1 times the reference value, it is considered that the antigen 62b of the high-concentration reagent remaining on the probe is cleaned and removed from the probe to a clinically sufficient level in the dispense/transfer system which dispenses the high-concentration reagent. Therefore, the identifying unit 45 determines that there is no cleaning defect in the dispense/transfer system which dispenses the high-concentration reagent. On the other hand, when the abnormality-identification measurement value is equal to or higher than 1.1 times the reference value, it is considered that the antigen 62b on the probe is not sufficiently removed and remains on the probe in the dispense/transfer system which dispenses the high-concentration reagent, and may affect the measurement result. Therefore, as indicated in table T2, the identifying unit 45 determines that there is a probe cleaning defect in the dispense/transfer system which dispenses the high-concentration reagent.

According to the second embodiment, the analyzer determines whether the substances in the previously-dispensed liquid are removed in the cleaning process of the dispense/transfer system to a clinically sufficient level or not, based on the reference value, i.e., the light-emission amount corresponding to the concentration of impurities which would not obstruct the output of clinically sufficient measurement result, and the abnormality-identification measurement value, i.e., the light-emission amount obtained by dispensing the zero-concentration reagent after actually dispensing the high-concentration reagent using the dispense/transfer system, for which the defect is to be identified. According to the second embodiment, processes other than the liquid dispense process of the dispense/transfer system, for which the abnormality is to be identified, are performed substantially in the same manner. Therefore, the contribution of other processes on the abnormality does not need to be considered, and the cleaning defect in the dispense/transfer system can be examined correctly. Further, according to the second embodiment, the presence/absence of the cleaning defect of the dispense/transfer system can be identified based on the measurement result obtained by the photometry system 31. Therefore, an independent spectrophotometer for calorimetric measurement is not required to be provided apart from the analyzer itself, unlike the conventional technology. Thus, according to the second embodiment, the abnormality of the analyzer can be identified correctly and easily.

In the second embodiment, in place of the low-concentration reagent, the high-concentration reagent, and the zero-concentration reagent containing as their component, the antigens reacting with the magnetic particle 61, the low-concentration reagent, zero-concentration reagent, and the high-concentration reagent containing as their component, the labeled substance reacting with the substrate (enzyme) acting as the light-emitting substrate may be employed. In this case, the analyzer 1 performs the reference-acquisition measurement process using a reagent containing labeled substances in predetermined very low concentrations as the low-concentration reagent. Further, the analyzer 1 performs the high-concentration-reagent use process using a reagent containing labeled substances in predetermined high concentrations as the high-concentration reagent, and then performs the abnormality-identification measurement process using the zero-concentration reagent containing no labeled substance.

Figure 19:
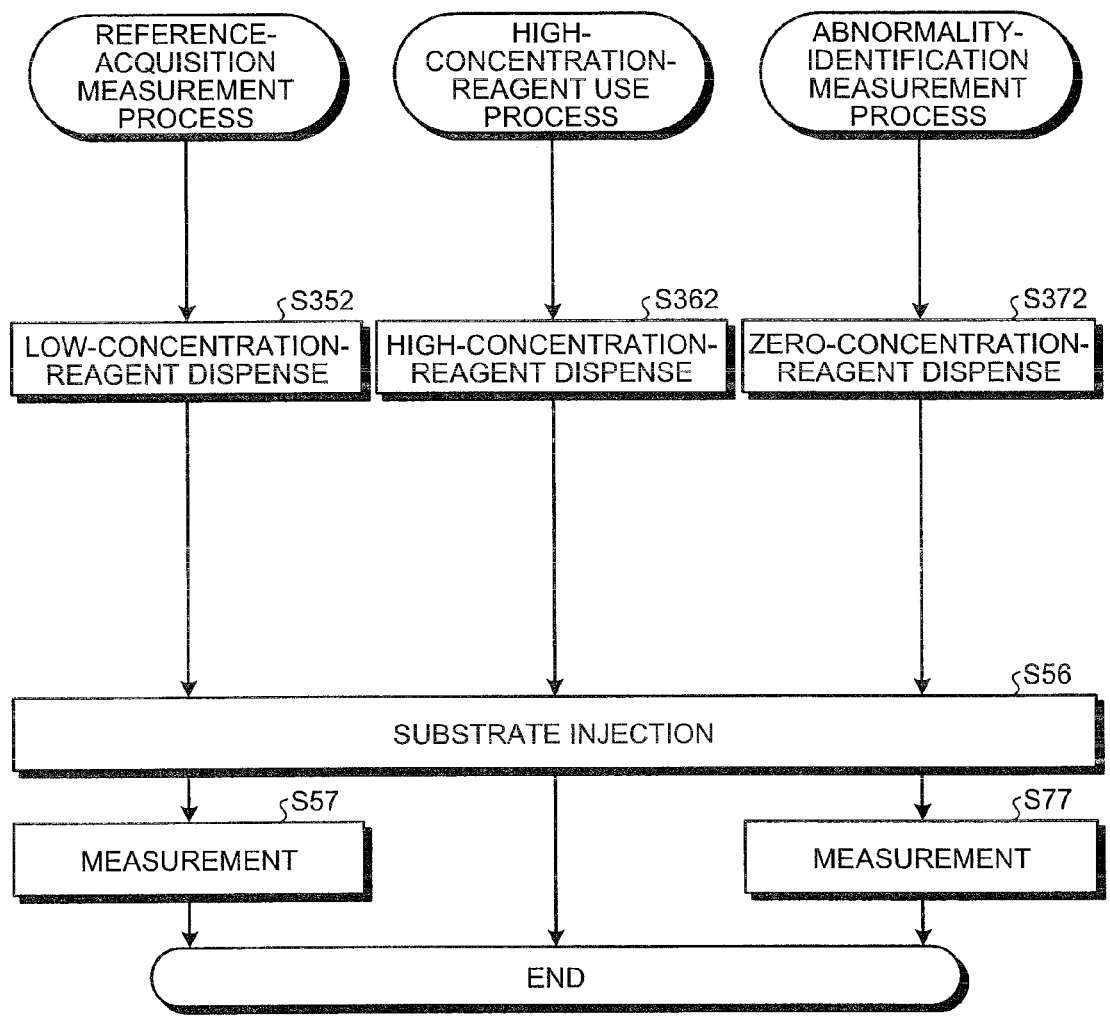
FIG. 19 is a flowchart of another example of process procedures of the reference-acquisition measurement process, the high-concentration-reagent use process, and the abnormality-identification measurement process illustrated in FIG. 12.
Figure 20:
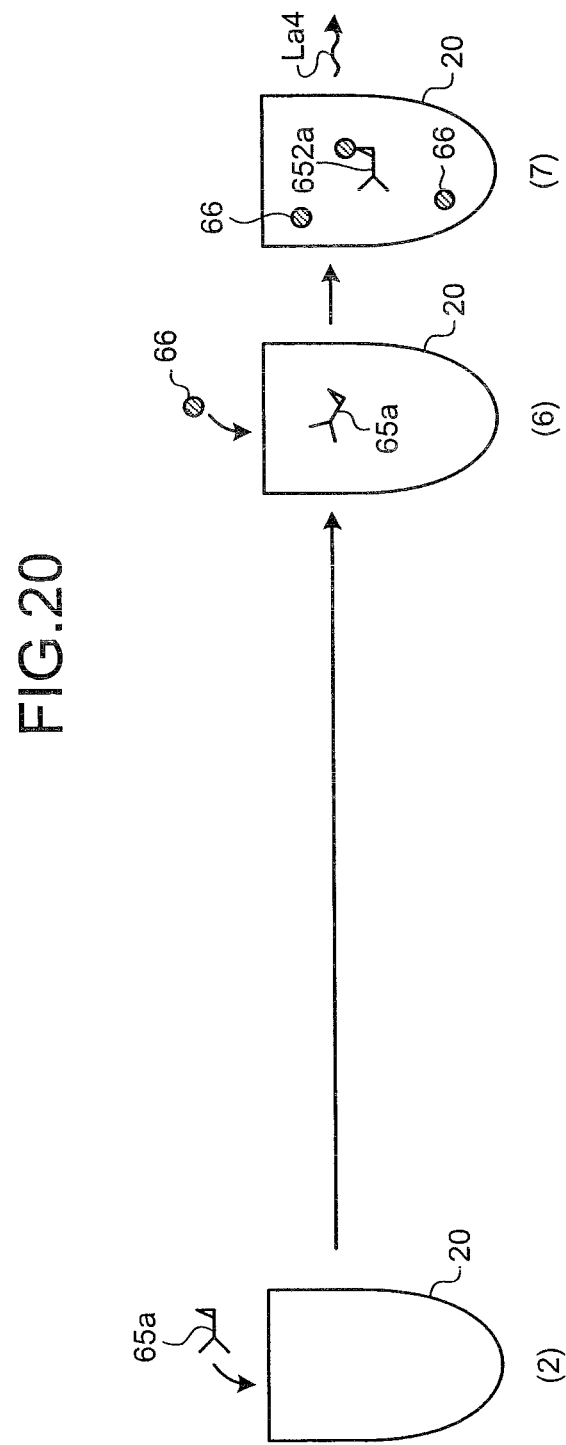
FIG. 20 is an explanatory diagram of the reference-acquisition measurement process shown in FIG. 19.

Following describes a case where the low-concentration reagent containing the labeled substance as its component is employed in the reference-acquisition measurement process shown in FIG. 19, with reference to FIGS. 19 and 20. As shown in FIG. 19 and (2) of FIG. 20, the low-concentration-reagent dispense process (step S352) is performed to dispense the low-concentration reagent containing the labeled antibodies 65a of, for example, 0.3 ppm to the buffer solution. Then, as shown in FIG. 19 and (6) of FIG. 20, the analyzer 1 performs the substrate injection process (step S56) to inject the substrate solution containing the substrate 66 to the cuvette 20 in order to acquire the light-emission amount corresponding to the labeled antibody 65a of 0.3 ppm as the reference value. After predetermined enzyme reaction, the substrate 66 and the labeled antibody 65a are bound with each other to form a bound substance 652a which emits light La4 as shown in (7) of FIG. 20. The analyzer 1 performs the measurement process (step S57) to measure the light La4, to thereby acquire the light-emission amount serving as the reference value. As shown in FIGS. 19 and 20, when the employed low-concentration reagent contains as its component, the labeled antibody 65a which is bound with the substrate 66 acting as the light-emitting substrate, the analyzer 1 can acquire the light-emission amount as the reference value simply through the enzyme reaction between the labeled antibody 65a and the substrate 66. In other words, when the employed low-concentration reagent contains the labeled antibody 65a as its component, the analyzer 1 does not need to perform processes required when the low-concentration reagent contains the antigen 62a to make the antigen 62a emit light. These processes include the process for injecting the magnetic particle 61, which is the first reagent (step S51), the process for injecting the labeled antibody 65, which is the second reagent (step S54), and the second BF cleaning process (step S55) for removing the labeled antibody 65 which is not bound to the magnetic particle carrier as illustrated in FIG. 13, and (1), (4), and (5) of FIG. 14.

Figure 21:
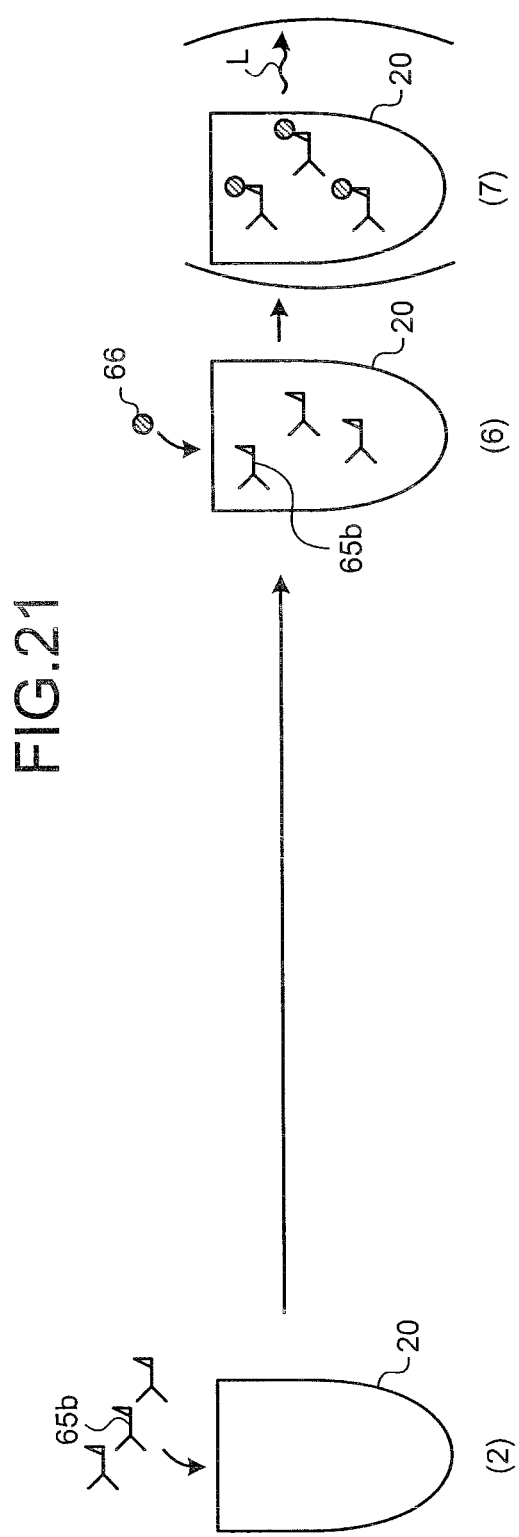
FIG. 21 is an explanatory diagram of the high-concentration-reagent usage process shown in FIG. 19.

Following describes a case where the high-concentration reagent containing the labeled substance as its component is employed in the high-concentration-reagent use process shown in FIG. 19, with reference to FIGS. 19 and 21. As illustrated in FIG. 19 and (2) of FIG. 21, the high-concentration-reagent dispense process (step S362) is performed to dispense the high-concentration reagent containing the labeled antibodies 65b of, for example, 1 million ppm into the buffer solution. Then, as illustrated in FIG. 19 and (6) of FIG. 21, the analyzer 1 performs the substrate injection process (step S56) to inject the substrate solution containing the substrate 66 into the cuvette 20 in order to make the labeled antibody 65b of 1 million ppm emit light. The labeled antibody 65b is bound to the substrate 66 and emits light L as illustrated in (7) of FIG. 21. However, the high-concentration-reagent use process finishes without measuring the light L. As shown in FIGS. 19 and 21, when the employed high-concentration reagent contains the labeled antibody 65b as its component, the analyzer 1 does not need to perform the process for injecting the magnetic particle 61 which is the first reagent (step S51), the process for injecting the labeled antibody 65 which is the second reagent (step S54), and the second BF cleaning process (step S55) for removing the labeled antibody 65 which is not bound to the magnetic particle carrier as illustrated in FIG. 13, and (1), (4), and (5) of FIG. 15.

Figure 22:
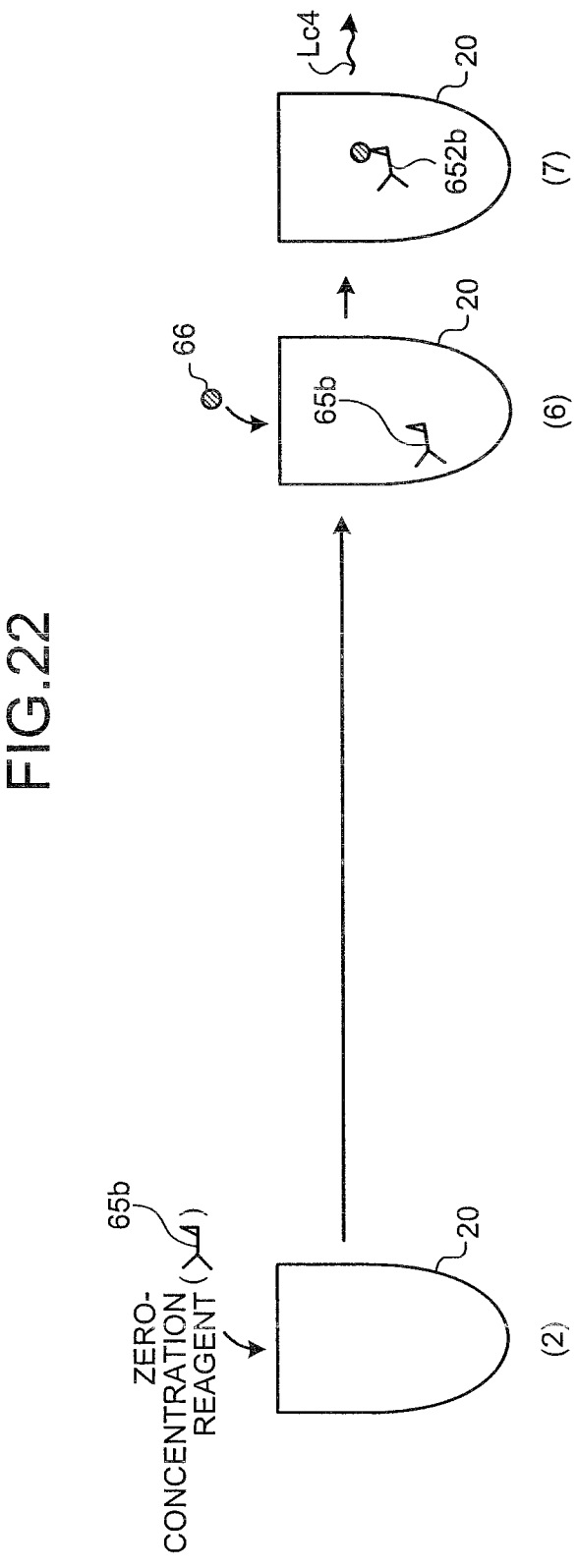
FIG. 22 is an explanatory diagram of the abnormality-identification measurement process shown in FIG. 19.

The abnormality-identification measurement process shown in FIG. 19 is described with reference to FIGS. 19 and 22. The analyzer 1 performs a zero-concentration-reagent dispense process (step S372) to dispense the zero-concentration reagent containing no labeled antibody as illustrated in FIG. 19 and (2) of FIG. 22. Then, the analyzer 1 performs an analysis process to make the labeled antibody 65b remaining on the probe and entering into the cuvette 20 in the zero-concentration-reagent dispense process emit light, and measures the abnormality-identification measurement value. Specifically, the analyzer 1 performs the substrate injection process (step S56) to inject the substrate solution containing the substrate 66 into the cuvette 20 as illustrated in FIG. 19 and (6) of FIG. 22. After the predetermined enzyme reaction, the substrate 66 and the labeled antibody 65b entered the cuvette 20 form a bound substance 652b which emits light Lc4 as illustrated in (7) of FIG. 22. The analyzer 1 performs the measurement process (step S77) to measure the light Lc4 to thereby acquire the light-emission amount serving as the abnormality-identification measurement value. As shown in FIGS. 19 and 22, when the zero-concentration reagent which does not contain the labeled antibody is employed in the analysis process to analyze the labeled antibody 65b remaining on the probe during the dispense process and entering into the cuvette 20, the analyzer 1 can acquire the light-emission amount, i.e., the abnormality-identification measurement value only through the enzyme reaction between the substrate 66 and the labeled antibody 65b which enters the cuvette 20 due to probe-cleaning defect. In other words, the analyzer 1 does not need to perform processes to make antigen 62b emit light when the zero-concentration reagent which does not contain the labeled antibody is employed in the analysis process to analyze the labeled antibody 65b remaining on the probe during the dispense process and entering into the cuvette 20. These process include the process for injecting the magnetic particle 61, which is the first reagent (step S51), the process for injecting the labeled antibody 65, which is the second reagent (step S54), and the second BF cleaning process (step S55) for removing the labeled antibody 65 which is not bound to the magnetic particle carrier as illustrated in FIG. 13, and (1), (4), and (5) of FIG. 16.

The analyzer 1 then identifies the abnormality in the probe-cleaning process by referring to the table T2 illustrated in FIG. 18 and comparing the reference value acquired as illustrated in (7) of FIG. 20, and the abnormality-identification measurement value acquired as illustrated in (7) of FIG. 22.

By using the low-concentration reagent, the high-concentration reagent, and the zero-concentration reagent containing the labeled substance as their component, the analyzer 1 can eliminate the second BF cleaning process as illustrated in FIG. 13, (5) of FIG. 14, (5) of FIG. 15, and (5) of FIG. 16 in the reference-acquisition measurement process, the high-concentration-reagent use process, and the abnormality-identification measurement process, whereby the analyzer 1 can identify the abnormality in the BF cleaning process even more promptly.

Further, when the low-concentration reagent, the high-concentration reagent, and the zero-concentration reagent containing the labeled antibody as their component are employed, the BF cleaning process is not required as illustrated in FIGS. 19 to 22. Therefore, even when there is an abnormality in the performance of the BF cleaning process to remove unreacted substances, the analyzer 1 can acquire the reference value and the abnormality-identification measurement value without being affected therefrom, and identify the abnormality in the probe cleaning even more accurately.

Further, as shown in FIGS. 19 to 22, the labeled antibody can be bound to the enzyme and emit light as it is. Therefore, when the low-concentration reagent, the high-concentration reagent, and the zero-concentration reagent containing the labeled antibody as their component are employed, the magnetic particle and the labeled antibody required for making the antigen emit light are not required. Hence, when the low-concentration reagent, the high-concentration reagent, and the zero-concentration reagent containing the labeled antibody as their component are employed, the analyzer 1 does not need to use the reagent containing the magnetic particle and the labeled antibody for identifying the abnormality in the probe-cleaning process, whereby the amount of reagent used for identifying the abnormality in the probe-cleaning process can be reduced.

The analyzer described in the above embodiment can be realized by a computer system such as a personal computer and a workstation, which executes predetermined programs. The computer system reads out programs stored in a predetermined storage medium to realize the procedure of the analyzer. The predetermined storage medium can be "a portable physical medium" such as a flexible disk (FD), a CD-ROM, an MO disk, a DVD disk, a magneto-optical disk, and an IC card, or a "communication medium" such as a hard disk drive (HDD), which is stored inside or outside the computer system, and temporarily stores programs therein for transmission of the programs, or any storage medium which can store computer-readable programs therein. The computer system obtains programs from other computer system which is connected therewith via a network, and executes the obtained programs to realize the procedure of the analyzer.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for determining a wash abnormality in an analyzer that measures an analyte, the analyzer having a plurality of wash stations, the method comprising:
   a) adding to a first cuvette a first magnetic particle that is not designed to react with the analyte;
   b) washing the first magnetic particle using a selected wash station;
   c) adding to the first cuvette a first amount of the analyte, a first labeled antibody, and a second magnetic particle that is designed to react with the analyte to form a first complex;
   d) washing the first complex using the selected wash station;
   e) measuring a first value corresponding to a signal from the first complex;
   f) adding to a second cuvette a second amount of the analyte and a third magnetic particle that is not designed to react with the analyte;
   g) washing the third magnetic particle using the selected wash station;
   h) adding to the second cuvette, a second labeled antibody, and a fourth magnetic particle that is designed to react with the analyte to form a second complex;
   i) washing the second complex using the selected wash station;

j) measuring a second value corresponding to a signal from the second complex; and k) determining that the wash process at the selected wash station is abnormal if the second value exceeds the first value by a predetermined multiple, wherein the first amount of the analyte is less than the second amount of the analyte.

2. The method of claim 1 wherein the signal from the first complex corresponds to a concentration of impurities which would not obstruct an output of a clinically sufficient measurement result.

3. The method of claim 1 wherein the first amount of the analyte corresponds to a low concentration of the analyte.

4. The method of claim 3 wherein the low concentration of the analyte is about 0.3 ppm.

5. The method of claim 4 wherein the second amount of the analyte corresponds to a high concentration of the analyte in the cuvette, and wherein the high concentration of the analyte is about 1 million ppm.

6. The method of claim 3 wherein the signal from the first complex comprises light generated by the first complex.

7. The method of claim 3 wherein the signal from the second complex comprises light generated by the second complex.

8. The method of claim 1 wherein the predetermined multiple is about 1.1.

9. The method of claim 1 wherein step b) includes washing the first magnetic particle using a first wash nozzle and washing the first magnetic particle using a second wash nozzle.

10. The method of claim 9 wherein step d) includes washing the second magnetic particle using the first wash nozzle and washing the second magnetic particle using the second wash nozzle.

11. The method of claim 10 wherein the predetermined multiple is about 1.2.

* * * * *